US007229505B2

(12) United States Patent
Hammock

(10) Patent No.: US 7,229,505 B2
(45) Date of Patent: *Jun. 12, 2007

(54) METHODS AND COMPOSITIONS FOR SURFACTANT-FREE CLEANING

(75) Inventor: Cory S. Hammock, Macon, GA (US)

(73) Assignee: Clean Control Corporation, Warner Robins, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/156,807

(22) Filed: Jun. 20, 2005

(65) Prior Publication Data

US 2005/0261154 A1 Nov. 24, 2005

Related U.S. Application Data

(60) Continuation-in-part of application No. 11/011,512, filed on Dec. 14, 2004, now Pat. No. 7,005,013, which is a division of application No. 10/078,010, filed on Feb. 19, 2002, now Pat. No. 6,835,704.

(60) Provisional application No. 60/652,158, filed on Feb. 11, 2005, provisional application No. 60/322,308, filed on Feb. 14, 2001.

(51) Int. Cl.
 *B08B 7/00* (2006.01)

(52) U.S. Cl. .......................... 134/40; 134/42; 510/108; 510/278; 510/280; 510/291; 510/384; 510/404; 510/434; 510/435; 252/8.81; 252/182.12; 252/183.12

(58) Field of Classification Search .................. 134/40, 134/42; 510/108, 278, 280, 291, 384, 405, 510/434, 435; 252/8.81, 182.12, 183.12
See application file for complete search history.

(56) References Cited

U.S. PATENT DOCUMENTS

| 4,035,148 | A | * | 7/1977 | Metzger et al. ................. 8/137 |
| 4,203,859 | A | | 5/1980 | Kirn et al. |
| 4,925,588 | A | * | 5/1990 | Berrod et al. ................ 510/299 |
| 5,510,047 | A | | 4/1996 | Gabriel et al. |
| 5,514,302 | A | * | 5/1996 | Brown ......................... 510/280 |
| 5,527,486 | A | * | 6/1996 | De Guertechin ............ 510/365 |
| 5,565,145 | A | | 10/1996 | Watson et al. |
| 5,566,145 | A | | 10/1996 | Sasaki |
| 5,643,861 | A | | 7/1997 | de Guertechin et al. |
| 5,679,631 | A | * | 10/1997 | Bohnert et al. ............. 510/411 |
| 5,718,729 | A | | 2/1998 | Harris |
| 5,904,735 | A | | 5/1999 | Gutierrez et al. |
| 5,905,065 | A | | 5/1999 | Scialla et al. |
| 5,928,384 | A | | 7/1999 | Scialla et al. |
| 5,929,007 | A | * | 7/1999 | Feng ........................... 510/197 |
| 5,962,391 | A | | 10/1999 | Oldenhove |
| 6,019,963 | A | | 2/2000 | Kling et al. |
| 6,171,346 | B1 | | 1/2001 | Yeazell et al. |
| 6,177,395 | B1 | | 1/2001 | Silvaggi et al. |
| 6,274,540 | B1 | | 8/2001 | Scheibel et al. |
| 6,403,547 | B1 | | 6/2002 | Grippaudo et al. |
| 6,407,048 | B1 | | 6/2002 | Grippaudo et al. |
| 6,605,579 | B1 | * | 8/2003 | Arvanitidou et al. ....... 510/235 |
| 7,005,013 | B2 | * | 2/2006 | Hammock ................... 134/40 |
| 2003/0215470 | A1 | | 11/2003 | Wilmott et al. |

OTHER PUBLICATIONS

J.C.T. Kwak, E.I., Polymer Surfactant Systems; Marcel Dekker: New York (1998).
E.D. Goddard and K.P. Anathapadhmanabhan. Ed., Interactions of Surfactants with Polymers and Proteins: CRC Press; Boca Raton, FL (1993).
Gauthire-Lafaye, J., and Gresser. R., Polymers in Detergency: AOCS 4$^{th}$ World Congress on Detergents: Rhodia. Courbevoic. France (1998).
Nagarajan, R., Polymer Surfactant Interactions: AOCS Presentation; Pennsylvania State University (2001).
Napper, D.H., Polymer Stabilization of Colloidal Dispersions. Colloid Science (1983).
Mandeep Singh Bakshi, Surfactant-Polymer Interactions Journal of Surfactants and Detergents, vol. 4, No. 1 (2001).
USEPA; Air Quality Criteria for Particulate Matter, vols. 1 and II; http://clpub.epa.gov/ncca/cfm/partmatt.efm (Oct. 2004).
USEPA; Child Exposure Factors handbook: EPA-600-P-00-002B http://oaspub.epa.gov/cims/cimscomm.getfile?p_download_id= 36528 (Sep. 2002).
PTL (DRAFT); Standard Test Practice Using X-Ray Fluorescence for Evaluating Cleaning Effectiveness of carpet Cleaning Processes (2004).
Mandeep Sing Bakshi: Polymer-Induced Incompatibility in the Mixed Micelle Formation of Cationic Surfactants . . . ; Journal of Surfactants and Detergents (2001), vol. 4, No. 3.
Sporik, R. et al. Mite, Cat, and Cockroach Exposure, Allergen Sensitization, Asthma in Children: A Case Control Study of Three Schools. Thorax (1999) pp. 675-680, vol. 54.
Standard Test Method for Accelerated Soiling of Pile Yarn Floor Covering, ASTM Designation No. D 6540-00, ASTM International, May 12, 2006.

* cited by examiner

*Primary Examiner*—M. Kornakov
(74) *Attorney, Agent, or Firm*—Kilpatrick Stockton LLP

(57) ABSTRACT

The present invention comprises methods and compositions for affecting indoor air quality, such as by reducing particulates in indoor air and providing allergen control comprising using surfactant-free cleaning compositions to remove particulate matter such as soils and stains from fibers and surfaces comprising fibers such as indoor carpeting and upholstery, and to prevent redeposition of particles and other soil or stain components on indoor environmental surfaces.

17 Claims, 3 Drawing Sheets

METHODS AND COMPOSITIONS FOR SURFACTANT-FREE CLEANING

RELATED APPLICATIONS

This application claims the priority of U.S. Provisional Patent Application No. 60/652,158, filed Feb. 11, 2005, and is a continuation-in-part of U.S. patent application Ser. No. 11/011,512, filed Dec. 14, 2004 now U.S. Pat. No. 7,005,013, which is a divisional application of U.S. Pat. No. 6,835,704, filed Feb. 19, 2002, which claims the benefit of U.S. Provisional Patent Application No. 60/322,308 filed Sep. 14, 2001, all of which are herein incorporated in their entireties.

TECHNICAL FIELD

The present invention relates to the field of cleaning compositions and to methods for using such compositions to affect indoor air quality such as particulate levels and aid in allergen control. The present invention is directed to surfactant-free cleaning compositions for use in removing soil and other particulate matter from carpets, upholstery and other fiber-based materials, as well as for preventing redeposition of soil and particulate matter on these and other surfaces, thus providing removal of particulates and allergen control through reduced potential for particle resuspension indoors.

BACKGROUND OF THE INVENTION

Indoor air pollution is a problem that is receiving much attention. Particulates in the air cause multiple problems, and include deposition of particulate matter in the airways, inhalation of toxic chemicals, metals and fibers that are present in the air, and exacerbation of allergic reactions in humans and animals. The presence of improperly maintained upholstery and carpets in confined spaces adds to the transmission and retention of particulates and allergens.

An allergen is a substance that causes an allergic reaction in an human or animal who is exposed to the substance. A comprehensive list of allergens is not possible, because sensitivities vary from person to person and it is possible for someone or an animal to be allergic to almost any substance.

A growing issue for children and adults is the increase in allergic asthma. In recent years, numerous hypotheses have advanced the biological plausibility for the exacerbation of allergic asthma likely associated with episodic exposure to allergens bound to soil particles, transported to lower tracheobronchial (TB) and alveolar (A) regions of the lung. Typically, allergens such as dander, including house mite, cockroach, cat, or dog allergens, or pollens such as ragweed, rye grass, or pine are found mainly in the coarse fraction of airborne particles. However, allergens can also be found in respirable particles that differ in particle size and chemical composition.

Recent studies show that all types of particles appear to exert an adjuvant effect on the immune response to co-administered protein antigen, indicating that inhaled antigen in particle-exposed individuals plays a major role in allergic asthma. Different particles stimulated distinct types of immune responses. Studies suggest that particles could modulate airway disease through their actions on airway epithelial cells and that bronchial epithelial cells from asthmatics are different from those of non-asthmatics.

Evidence also suggests that metals commonly found in particulate matter are responsible for augmentation of allergic sensitization and may be responsible for increased allergic sensitization in treated animals. Increased concentrations of heavy metals have been found in the body tissues (including lungs) of humans and other mammals living in areas with elevated metal-containing soils.

The body in response to acute injury, infection, or other inflammatory stimuli releases C-reactive protein (CRP) and cytokines. This response is called the acute phase reaction. Acute phase proteins are a class of proteins that are synthesized in the liver in response to inflammation. C-reactive protein is a special type of protein produced by the liver that is only present during episodes of acute inflammation. CRP is therefore a marker of inflammation. The most important role of CRP is its interaction with the complement system, which is one of the body's immunologic defense mechanisms.

Cytokines are small protein molecules that are the core of communication between immune system cells, and even between immune system cells and cells belonging to other tissue types. They are actively secreted by immune cells as well as other cell types. Their action is often local, but sometimes can have global effects on the whole body. Cytokines act by binding to their cell-specific receptors. These receptors are located in the cell membrane and each allows a distinct signal cascade to start in the cell, which eventually will leads to biochemical and phenotypical changes in the target cell.

It has recently been discovered that CRP also plays a role in heart disease. Atheromatous plaques, characterized by thickening and fatty degeneration of the inner coat in diseased arteries, typically contain inflammatory cells. Rupture of atheromatous plaque is thought to be the mechanism for acute myocardial infarction and acute coronary syndrome. The most common site of plaque rupture appears to be the shoulder region where inflammatory cells are most prominent. Thus the release of acute phase reactants as a response to inflammation have been proposed as a potential marker of an "unstable" atheromatous plaque and underlying atherosclerosis, the progressive narrowing and hardening of the arteries over time.

The amount of CRP produced by the body varies from person to person, and this is affected by an individual's genetic makeup. Higher CRP levels tend to be found in individuals who smoke, have high blood pressure, are overweight and don't exercise, whereas lean, athletic individuals tend to have lower CRP levels.

The toxicological consequences of inhaled particles on the cardiovascular system are also under increased investigation. The studies suggest that pathophysiological changes in cardiac function, such as heart rate variability, post-myocardial infarction; increased atherosclerosis plaque formation and/or blood coagulation could be linked to inhaled protein and other toxins found in respirable metal-associated particles.

What is needed are improved methods for improving indoor air quality such as in control of particulates in indoor air and reduction in allergen exposure by humans, adults and children, and animals.

SUMMARY

The present invention comprises methods for affecting indoor air quality such as reducing particulate matter and allergens, and compositions for accomplishing same. The methods of the present invention comprise methods of applying compositions that result in reduction of particulates in indoor air, reduction of toxic materials in indoor air and reduction of allergens in indoor air. The present invention also comprises methods for treating and preventing allergic conditions, cardiology-related conditions and other conditions related to particulate and toxic material exposure. The compositions of the present invention are taught herein and in U.S. Pat. No. 6,835,704, which is incorporated in its entirety.

Methods of the present invention comprise applying the compositions of the present invention to the surfaces and fibers, the surfaces of fabrics and materials made with fibers, including but not limited to carpet, upholstery or drapery fabrics, and other surfaces, and removing at least a portion of the composition having soils and other particulate matter removed from those fibers and surfaces dispersed therein. The compositions of the present invention are particularly useful in preventing the redeposition of particulates during cleaning, thus reducing the amount of particulates in the environment.

DETAILED DESCRIPTION

Figure 1:
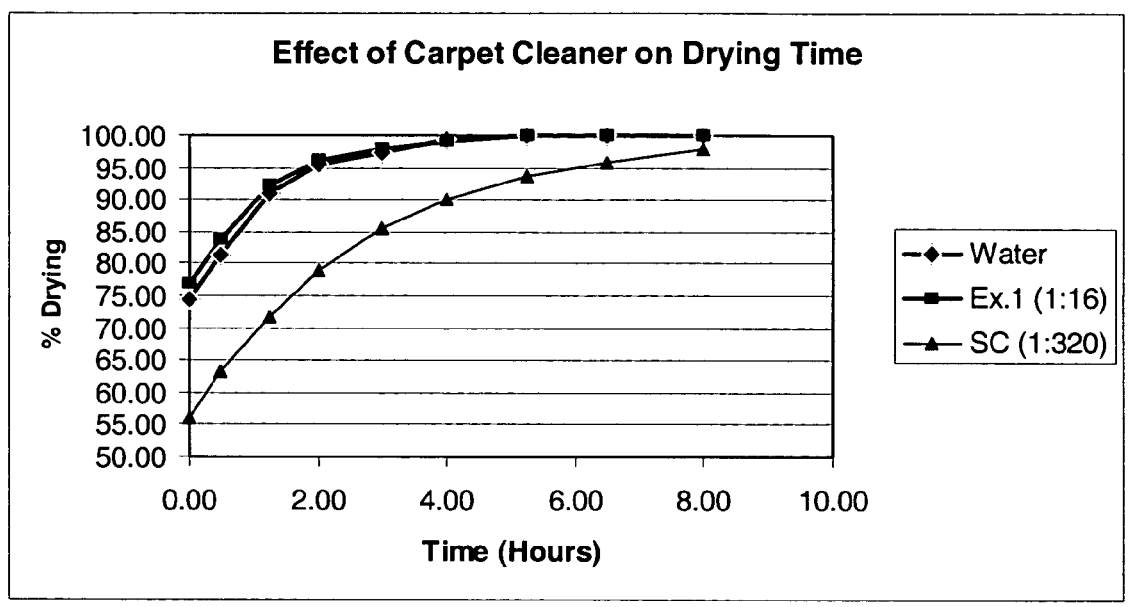
FIG. 1 is a graph showing the effect of compositions on drying time of a carpet.

The present invention comprises methods for affecting indoor air quality. Methods comprise reducing particulate matter and allergens in the air and on surfaces, and compositions for accomplishing same. The compositions of the present invention comprise surfactant-free cleaning compositions. The methods of the present invention comprise methods of applying compositions that result in reduction of particulates in indoor air, reduction of toxic materials in indoor air and reduction of allergens in indoor air. The present invention also comprises methods for treating and preventing allergic conditions, cardiology-related conditions and other conditions related to particulate and toxic material exposure by removing particulate matter from the environment of the subject and reducing the exposure of the subject with allergic conditions, cardiology-related conditions and other conditions, to particulate matter. The compositions of the present invention are taught herein and in U.S. Pat. No. 6,835,704, which is incorporated in its entirety.

The compositions of the present invention are effective for removal of particulates from fibers, surfaces comprising fibers, and other surfaces. Methods of the present invention also comprise using such compositions on fibers and surfaces comprising fibers that have not been exposed to surfactant-containing compositions. Methods may also comprise multiple treatments of fibers or materials made with fibers. For example, if the fibers or surfaces comprising fibers have been treated or exposed to surfactant-containing compositions, the methods may comprise treatment steps of the fiber or surfaces comprising fibers comprising one or more application of the compositions of the present invention. to remove residues of the surfactant-containing compositions from the surfaces. Methods of the present invention comprise using such compositions on surfaces comprising fibers that may or may not have been exposed to surfactant-containing compositions.

Methods of the present invention comprise treatments for fibers, materials comprising fibers, surfaces comprising fibers, and other surfaces. As used herein fibers and surfaces means fibers, materials made from fibers, materials comprising some amount of fibers, woven and nonwoven materials, upholstery fabrics, rugs, carpeting, padding, mats, drapery fabrics, table linens, and materials made of fibers and fabrics, such as those found in interior environments. Fibers and surfaces also includes surfaces of materials that are not made of fibers that are found in indoor or interior environments for which preventing redeposition of particulate matter is useful, including but not limited to, flooring, furniture surfaces, countertops, walls, trim and other surfaces found in indoor environments. Treatment of fibers and surfaces may comprise removal of particulate material from a portion or the entire length of the fiber, from the surface of the fiber, from a padding material adjacent to a fiber-containing material, and from smooth and rough surfaces. Fibers may be natural or synthetic fibers, and includes combinations and mixtures of natural and synthetic fibers, and combinations and mixtures of one or more natural or one or more synthetic fibers. Natural fibers include, but are not limited to, silk, wool, cotton, mohair, cashmere, linen, flax fibers, ramie, hemp, jute, sisal, kapok, and other fibers made by or derived from animals, plants, insects and other living organisms. Synthetic fibers include, but are not limited to, various polyesters, nylons, rayon, arnel, cellulose, acetates, acrylic, modacrylic, olefin, vinyon, saran, metallic fibers, spandex, aramids, PBI, sulfar, and other synthetic materials that can be made into fibers. Surfaces comprising fibers include, but are not limited to, carpets of all types, sizes, and uses, such as area rugs or wall-to-wall carpeting, felts, and fabrics used in indoor or outdoor environments, including but not limited to upholstery, linens, and drapery fabrics. Surfaces that do not contain fibers may also be treated with the compositions of the present invention, but the benefits of particulate and allergen control are most noted in treatment of surfaces comprising fibers. As is known, such fibers and surfaces may be located in interior or exterior environments, and the compositions and methods of the present invention are effective on such fibers and surfaces where ever located. An interior environment is generally considered to be indoors and an exterior environment is generally considered to be outdoors.

Though not wishing to be bound by any particular belief, it is believed that the compositions of the present invention are effective at removal of particulate material by dispersing the particles present on a fiber or surface and lifting the particle off of the fiber or surface, holding the particle in the liquid portion of the composition, referred to herein as dispersing the particle, preventing the particle from reassociating with the fiber or surface by remaining in the liquid, and being removed from the area by removing some amount of the liquid portion of the composition. By combining dispersing, dissolution and anti-redeposition of charged and other particles without wetting the fiber or surface, and the associated soil spreading problems, the present invention overcomes problems which have been encountered with surfactant-containing cleaning compositions containing micelle forming surfactants. For example in carpeting applications, surfactant-containing cleaning compositions overcome stain prevention chemicals present on the carpet fibers and allow water to penetrate into the fiber, and allow water to penetrate further down the length of the fibers towards, and into the padding of the carpet. The soil or dyes are carried into the fiber, down the fiber or into the padding by the water, which then stains the fibers of the carpet or requires higher pressure removal techniques to withdraw the penetrated water and soil or dyes. The present invention comprises compositions and processes for removal of metal-associated soils from fibers and materials comprising fibers and reduces the human and animal exposure to such soils and other particulates commonly found in indoor environments.

The compositions and methods of the present invention are effective in removing particulates from surfaces and are particularly effective in indoor or interior environments where particulate matter is present in high amounts. For example, indoor environments where persons smoke, fires are used for heating or cooking, during periods of high pollen count or dust count, or high traffic areas where humans, animals and others track soil and other particulate matter into the interior environment on a regular or frequent level. For example, many commercial and industrial locations where there is frequent traffic can be treated with the present invention, including, but not limited to, all means of public transportation, airplanes, trains, subway trains, taxis, buses, cars, malls, concert halls, public buildings, bars, hotels, motels, condominiums, apartments, day care facilities, elderly facilities, meeting halls, cinemas, theaters, physician offices, hospitals, kennels, and veterinary hospitals, and other areas where humans, animals or other carriers of soils, particulate matter, or smoke walk, ride or repose. Methods of the present invention comprise applying the compositions of the present invention to surfaces, including fibers and materials comprising fibers, present in interior environments having high amounts of particulate matter, and removing the composition after an amount of the particulate matter has admixed with the composition. Such applications may occur one or multiple times and determining the number of applications is dependent on the amount of particulate matter present and the degree of removal desired.

An aspect of the present invention comprises a surfactant-free, aqueous cleaning composition comprising polymeric dispersing agents, polymeric anti-redeposition agents and a sufficient amount of an alkali counter ion to maintain the pH of the aqueous composition in a range of about 5.0–12.0, generally 9.0–10.0. In this regard, it has been found that such compositions have the advantage of demonstrating soil suspending activity without the use of micelle-forming surfactants found in prior art carpet and upholstery cleaning products. This is a commercial advantage since products containing the micelle-forming surfactants have received low customer satisfaction ratings due to problems relating to their use. Surfactants cause dyes and other materials penetrate and react with fibers, creating stains that cannot be removed, and cause dyes and other materials to move from the surface of the material to deeper regions in the material, such as in a padding, and then migrate back up the fibers, thus a stain will reappear once the material dries. Surfactants also interfere with fiber treatments, such as relaxing the individual fibers in a strand, or removing kinks or bends in a fiber and thus changing the appearance of the fibers, or altering the pile characteristics. The present compositions, with their absence of micelle-forming surfactants, are effective at stain removal and particulate material removal; as well as, removal of residual surfactants left by previous cleanings with compositions comprising surfactants, which have a negative impact on the inherent carpet and upholstery anti-soil properties. Residual surfactants left by applications of compositions comprising surfactants allow for dye and particulate matter to adhere more easily and with greater attachment force than new, untreated or fibers and adjacent materials which have never had surfactants applied.

Further advantages of the present invention, which relate to enhanced soil removal, when compared to prior-art surfactant-based cleaners, include reduced allergic allergen sensitization exacerbated by particulates such as metals, found in common household soil particles. It is currently believed that microscopic sized particles of metals, found in soil and other particulate matter, aid in retention of particulate matter, such as allergens and exacerbate pathological conditions such as allergen-related conditions. Metal particulates act in two ways. In one way, metal particulate materials act by a catalytic effect by attaching to charged particles such as allergens like pollen and dander, and agglomerating them to form particle sizes that are inhaled and retained by the lungs. The present invention removes the metal/allergen agglomeration and reduces the overall particulate exposure level in the environment. It is thought that particles from 0.1 micron to 1 micron are of a size that is more likely to adhere in the lung and create allergic-related, cardiac, carcinogenic and other pathological conditions in humans and animals. Metals are also involved in retaining other particulate matter in the environment. The presence of metal particulates in the environment leads to retention of other particles that may not have been retained, had the metal particulates not been present. Thus metal particulates have a synergistic effect in increasing the load of particulate matter that can exist in an environment, particularly associated with fibers, materials comprising fibers, and other surfaces in the environment. Though the invention is effective in removal of particulates in interior environments, particulates in exterior environments are also effectively removed, and applications of the compositions to any surfaces, wherever found, are contemplated by the present invention.

It is an object of the present invention to overcome the problems which have been encountered with prior art surfactant-containing cleaning compositions including, wetting and soil spreading problems which have been encountered employing previous cleaning compositions containing micelle forming surfactants. The present invention also overcomes problems of surfactant-containing compositions in particulate removal.

Sections 7.5.3 and 7.9 of the Air Quality Criterion for Particulate Matter (October 2004), Volume II discuss information about airborne particles as carriers of toxic agents in detail. These studies indicate that improved removal of metal contaminates and naturally occurring soils from carpet and upholstery reduce the potential for allergic allergen sensitization. Studies have suggested that factors other than allergen concentrations play a major role in determining the amount of allergen necessary to sensitize atopic children. Dust and tracked-in soil accumulates in carpets and upholstery, where young children spend a significant amount of time.

Major sources of indoor metal-associated soils in non-smoking residences include ambient outdoor particulate matter and tracked in soil. Human and pet activities are also sources of particulate matter that is found ubiquitously on and in house dust deposited on floors, draperies, carpets, home furnishings and other interior surfaces. Indoor metal-associated soils may be resuspended after deposition on indoor surfaces by human activities such as cleaning and walking. Typically, resuspension of soils from any source involves coarse particles (>1 µm). Indoor activities account for 50–90% of coarse particle (>1 µm) concentrations. Typically, children are exposed to higher concentrations because children are on the floor more than adults, and are generally shorter, thus closer to the floor where indoor air concentrations would be anticipated to be higher in closer proximity to the source of the soil.

Table 1

A copy of Table 5–11 of the Air Quality Criterion for Particulate Matter (October 2004). Volume II describes the Volume Mean Diameter (VMD) and Maximum $PM_{2.5}$ concentrations of indoor air particle sources.

TABLE 5-11

VOLUME MEAN DIAMETER (VMD) AND MAXIMUM $PM_{2.5}$ CONCENTRATIONS OF INDOOR PARTICLE SOURCES[a]

| Particle Source | Size Statistics | Maximum Concentration ($PM_{2.5}$) | |
| --- | --- | --- | --- |
| | Mean VMD (µm) | Mean (µg/m³) | SD (µg/m³) |
| Dusting | 5.38 | 22.6 | 22.6 |
| Vacuuming | 3.86 | 6.5 | 3.9 |
| Walking Vigorously (w/Carpet) | 3.96 | 12.0 | 9.1 |
| Sampling (w/Carpet) | 4.25 | 8.0 | 6.6 |
| Sampling (w/o Carpet) | 4.28 | 4.8 | 3.0 |

[a]All concentration data corrected for background particle levels.

While particle deposition and retention in the respiratory tract is influenced by complex physical; as well as anatomical and physiological factors, one critical factor is particle size. Particles deposit within the respiratory tract by five mechanisms: (1) inertial impaction, (2) sedimentation, (3) diffusion, (4) interception, and (5) electrostatic precipitation. Particles are continuously influenced by gravity, but coarse particles (>1 µm) are affected to the greatest extent.

Inertial impaction is a significant deposition mechanism for particles larger than 2 µm. Both inertial impaction and sedimentation can influence the deposition of particles within the same size range. These deposition processes act together in the ET and TB regions. Inertial impaction dominates in the upper airways, and gravitational settling becomes increasingly dominant in the smaller conducting airways. Particles having actual physical diameters <1 µm are increasingly subjected to diffusion deposition because of random bombardment by air molecules, resulting in contact with airway surfaces. Interception is deposition by physical contact with airway surfaces. Fibers are of chief concern in relation to the interception process.

The particle size range around 0.2 to 1.0 µm is frequently described as consisting of particles that are small enough to be minimally influenced by impaction or sedimentation and large enough to be minimally influenced by diffusion. Such particles are the most persistent in inhaled air and undergo the lowest degree of deposition in the ET and TB regions of the respiratory tract, thereby reaching the alveolar (A) regions of the lung.

Electrostatic precipitation is deposition related to particle charge. The electrical charge on some particles will result in an enhanced deposition over what would be expected from size alone. The effect of charge on deposition is inversely proportional to particle size and airflow rate. This type of deposition is often small compared to the effects of turbulence and other deposition mechanisms, and it generally has been considered to be a minor contributor to overall particle deposition.

Particles may be classified as inhalable, thoracic, and respirable particles. Inhalable particles enter the respiratory tract. Thoracic particles travel past the larynx and reach the lung airways and the gas-exchange regions of the lung. Respirable particles are a subset of thoracic particles that are more likely travel past the extrathoracic (ET) region to reach the gas-exchange (A) region of the lung.

Accumulation mode particles in the region between 0.001 and 3.0 µm are formed primarily by combustion or chemical reactions of gases. Accumulation mode particles are composed of metals (and metal oxides), black or elemental carbon, primary and secondary organic compounds, sulfate, nitrate, ammonium and hydrogen ions. Coarse mode particles in the region between 1 and 100 µm are formed by the mechanical breakdown of minerals, crustal material, and organic debris. In addition to primary minerals and organic material, the coarse mode may include sea salt, nitrate formed from the reaction of nitric acid with sodium chloride, and sulfate formed from the reaction of sulfur dioxide with basic particles.

The ET, TB and A region deposition is a minimum between 0.1 and 1 µm diameter (the accumulation mode size range) and increases for larger (coarse mode) and smaller (ultrafine particle) size ranges. For ultrafine particles, alveolar (A) region deposition peaks between 0.01 and 0.1 µm and TB deposition increases as particle size decreases below 0.1 µm.

Figure 2:
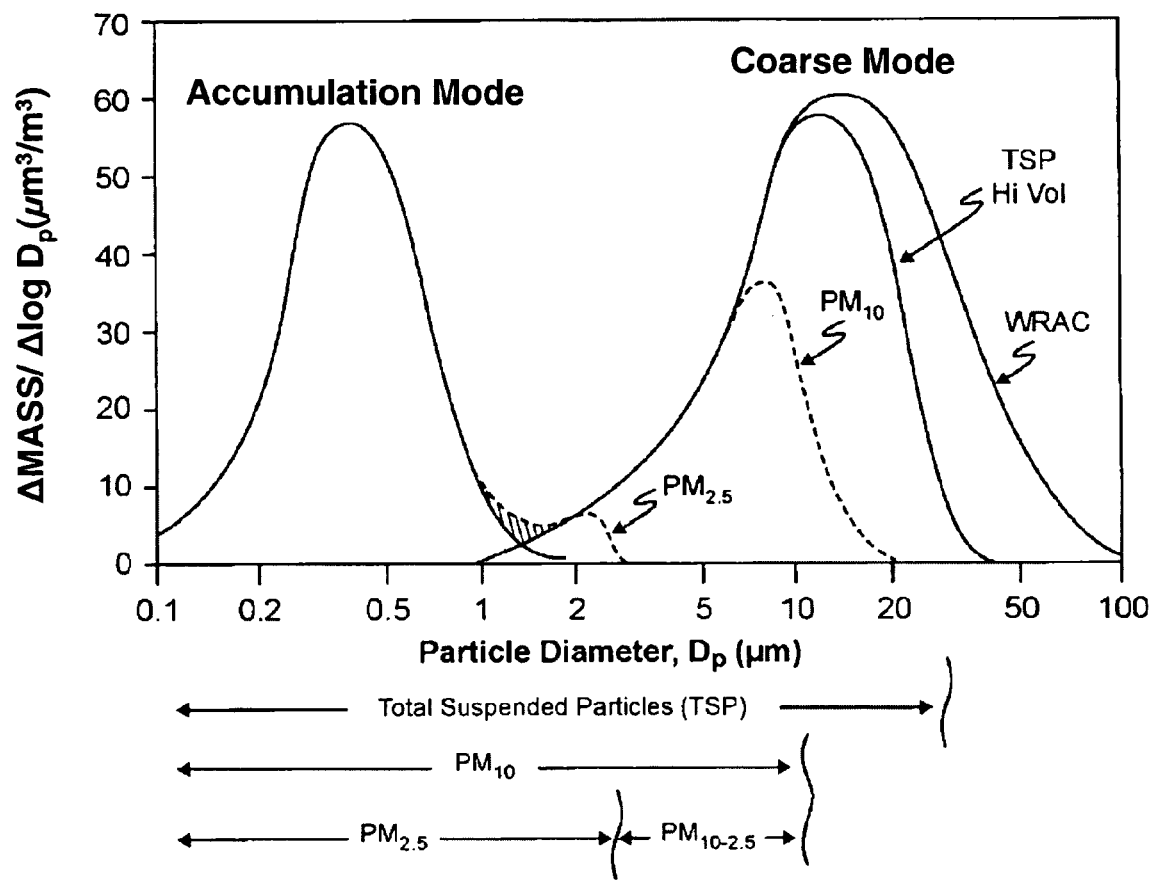
FIG. 2 is a graph showing particulate sizes.
Figure 3:
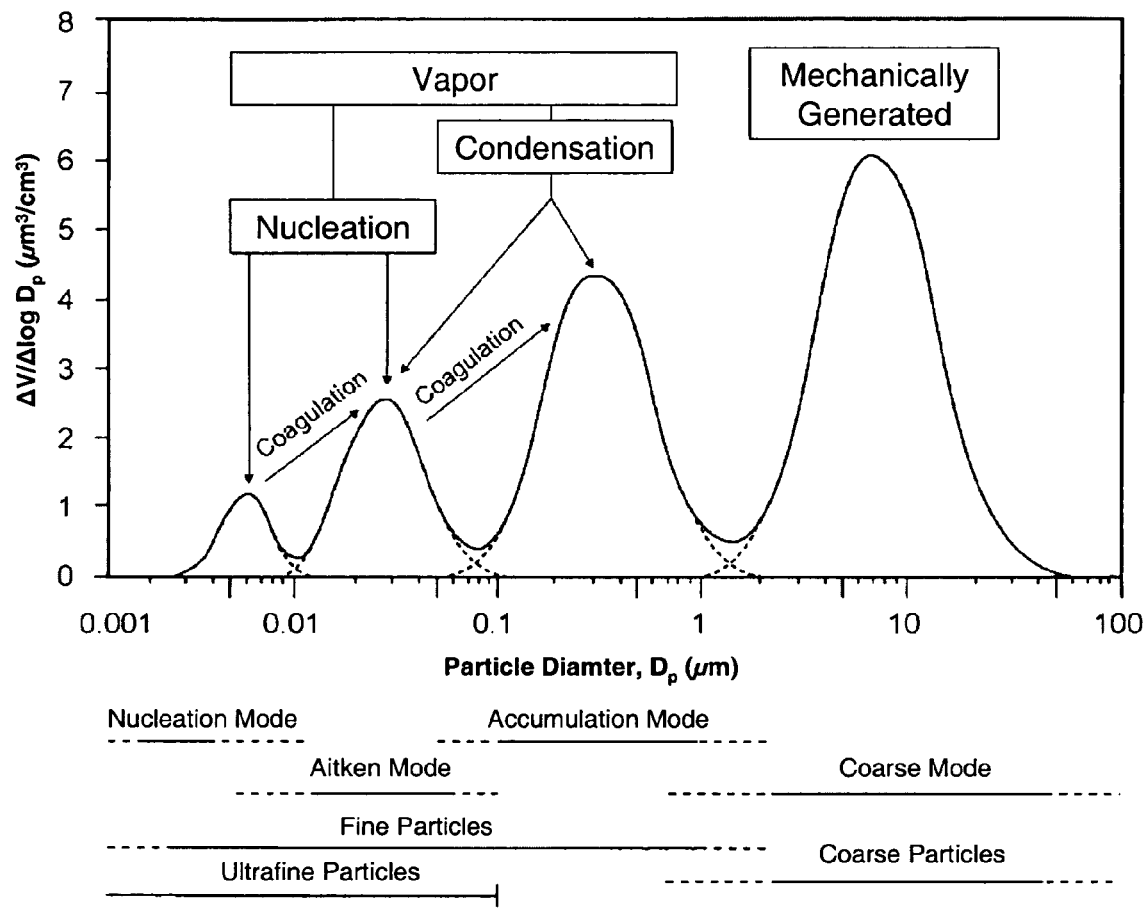
FIG. 3 is a graph showing an idealized size distribution of particulates.

See FIG. 2 for a graph showing the distribution of ambient particulate matter showing accumulation mode particles and coarse mode particles and the fractions collected by size-selective samplers. This graph is an adaptation of Wilson and Suh (1997) and Whitby (1978). The accumulation mode and the coarse mode particles overlap in the region between 1 and 3 µm (and occasionally over an even larger range). In this region, the chemical composition of individual particles usually, but not always, allows identification of a source or formation mechanism, permitting identification of a particle as belonging to the accumulation or coarse mode. In FIG. 2, WRAC is wide range aerosol classifier. FIG. 3 shows an idealized distribution of particulates, that might be observed in traffic, showing fine and coarse particles, and the nucleation, Aitken, and accumulation modes that comprise fine particles. Also shown are the major formation and growth mechanisms of the four modes of atmospheric particles.

Accumulation mode and coarse mode particles differ not only in size but also in formation mechanisms, sources, and chemical, physical, and biological properties. Transition metals in coarse particles are likely to be associated with soil and tend to be less soluble (and presumably less bioavailable) than transition metals in fresh combustion particles found in fine particles.

Accumulation mode particles in the middle of size range (0.2 to 1.0 µm) have the lowest deposition fraction in the ET and TB regions. The fractional deposition of ultrafine particles in the A region peaks between 0.02 and 0.03 µm and is greater than predicted for both accumulation and coarse mode particles. For coarse particles, fractional deposition peaks between 4 and 6 µm for the TB region and between 2.5 and 5 µm for the A region. A significant fraction of ultrafine and coarse particles, but not particles in the accumulation-mode size range, are deposited in the ET region. Once particles are deposited on the surface of the airways, they are subsequently cleared from the respiratory tract or translocated to other sites within the system by distinct regional processes. Particle deposition is enhanced in people with chronic lung disease.

Poorly soluble particles deposited in the TB region are cleared by mucociliary transport towards the oropharynx, followed by swallowing. Soluble particles may be absorbed through the epithelium into the blood, and may travel to organs outside of the lungs. Solubility is influenced by the particle's surface to volume ratio and other properties such as hydrophilicity and lipophilicity. It has been shown that decreased bronchial flow is associated with increased airway retention of soluble and non-soluble particles. Prolonged exposure to high concentrations of relatively nontoxic, poorly soluble particles is associated with a phenomenon termed particle overload. Moreover, there is a significant relationship between particle dose, expressed as particle surface area/lung, and chronic inflammation and increased translocation of particles in the interstitium.

Particle deposition in the TB region is less harmful than in the A region because clearances in the TB region are more rapid and the epithelium is protected by a mucous layer. As a result, poorly soluble particles may harm the alveoli while soluble particles may not reach this region.

The mechanisms of action and ultimate biological effects of inhaled particles and the proximal cause of the biological response are due to the dose of particles delivered to and retained at the target site, rather than the exposure concentration. Deposition, clearance, and retention comprise the essential elements of particle exposure measurement. Properly characterizing the inhalation of particles is essential to understanding the effects observed in human exposure studies and for relating effects in healthy individuals to those in potentially susceptible persons. The extrathoracic (ET) region, especially the nasal passages, is an efficient filter for ultrafine (<0.01 μm) and larger coarse particles, but filtration is less efficient for larger ultrafine and fine particles.

Accordingly, particles removed in the ET region are not available for deposition in the tracheobronchial (TB) and alveolar (A) regions of the respiratory tract. Within the thoracic region, the deposition distribution of ultrafine particles (0.01 to 0.1 μm) is highly skewed towards the proximal airway regions and resembles that of coarse particles. Thus, the deposition patterns for ultrafine particles are similar to those of coarse-mode particles, with significant fractional deposition in all three regions. Particles in the accumulation mode size range (0.1 to 1.0 μm) have lower fractional deposition in all three regions. The dose information expressed by fractional deposition may be applied only to acute exposure conditions. Retained dose at any given time is determined by the balance between deposition and clearance. In this regard, a long-term retained dose can be much greater than an acute exposure dose in individuals with impaired clearance mechanisms.

The present invention is effective at removal of particulate material from interior environments and removal of particulate material classified as accumulation mode and coarse mode sizes are contemplated. Methods of the present invention comprise applying the compositions of the present invention to fibers, materials comprising fibers, and other surfaces using fabric cleaning devices and methods such as home, industrial or truck mounted carpet cleaning machines, hand cleaning methods, upholstery cleaning machines, steam or fluid applicators, mops, and combined with removal mechanisms such as vacuum or suction, removing from the fibers or other surfaces, particulate material having a size from 0.001 μm to 100 μm.

Methods of the present invention comprise applying a liquid surfactant-free composition to a fiber, allowing sufficient time for the particulate matter, including particles and dyes, to disperse within the composition, and removing the composition from the fiber. By applying, it is meant that the composition contacts the fiber. Other associated materials may also be contacted by the composition, such as backing material, pads, or materials to which the fibers may be attached or interwoven. By the particulate matter dispersing within the composition, it is meant that the particulate matter including but not limited to, particles and dyes, are more associated with the composition and less associated with the fiber or surface. The particulate matter may or may not dissolve in the liquid composition and may be admixed in the liquid or with components of the composition. Before applying the composition the particulate matter is found associated with the fiber, and after applying the composition, the particulate matter is found associated with the composition. The method may be repeated until the desired amount of particulate matter is removed.

Chemical reactions in the indoor environment are responsible for secondary particle formation and modification of existing particles. This process is complex and may influence exposures to indoor-generated particles. For example, terpenes (specifically d-limonene, α-terpinene, and α-pinene) have been found to react with ambient ozone, resulting in a 10-fold increase in fine particles (0.1 to 0.2 μm). Ozone ($O_3$) appears to be the limiting reagent because particle number concentration varies proportionally to $O_3$ concentrations. However, concentration would also depend on the $O_3$ infiltration factor and the indoor generation rate of terpenes. Ambient $O_3$ and ambient $PM_{2.5}$ are correlated in the summertime; indoor-reaction particles due to $O_3$-terpene reactions might be correlated with outdoor $PM_{2.5}$ mass. $PM_{2.5}$ (particulate matter) is indicated in FIG. 2. Such particles, if toxic, would represent an increased health risk due to ambient indoor air pollution. It seems more appropriate to consider indoor-reaction particles as part of non-ambient exposure. Therefore, carpet and upholstery cleaners that are intended to reduce the potential for particle resuspension indoors should contain a minimum quantity of terpenes or similar chemicals.

The compositions of the present invention, comprising a liquid, surfactant-free composition, reduce the potential for particle resuspension indoors by removing particles in the range of from about 0.001 μm to about 100 μm, from about 0.03 to about 5.0 μm, from about 0.1 μm to about 50 μm, from about 0.001 to about 2.0 μm, from about 1.0 μm to about 20 μm, from about 1. μm to about 20 μm, from about 1.0 μm to about 50 μm, from about 1.0 μm to about 100 μm, and from less than about 0.1 to about 100 μm, and optionally, do not contribute to the formation of particles of the same size. Recent advances in carpet cleaning efficacy testing have focused on removal of metal-associated soils containing an exact quantity of elements chosen for particle size and chemical characteristics naturally occurring in soil. The results of the quality assured composition and cleaning efficacy data are obtained by X-ray fluorescence (XRF).

Compositions of the present invention comprise surfactant-free, aqueous cleaning compositions comprising a polymeric dispersing agent, a pH modifier, and a polymeric anti-redeposition agent. The compositions may optionally further include ingredients such as chelating agents, fragrance materials, stabilizing agents, and preservative agents, and may depend on the state of the compositions, solid liquid or gel, or when the composition is admixed.

Exemplary of suitable polymeric dispersing agents for use in the compositions of the present invention are polymeric and co-polymeric compounds such as polyacrylic acid, polyacrylic acid/maleic acid copolymers; styrene/maleic anhydride copolymers, polymethacrylic acid, polyaspartic acid and the like, including combinations or mixtures of two or more of these. Water soluble compounds are useful in aqueous solutions or compounds that are sufficiently soluble at the volumes and pH of the composition.

Exemplary of suitable polymeric anti-redeposition agents for use in the compositions of the present invention are polymeric and co-polymeric compounds such as polyvinylpyrrolidone, polyvinylbetaine; polyvinyl pyrrolidone/vinylacetate copolymers, polyvinylpyrrolidone/ dimethylamino-ethylmethacrylate copolymers, polyvinylpyrrolidone/acrylic acid copolymers, polymethylvinylether/maleic anhydride copolymers; polyvinylpyridine-n-oxide and the like which form complexes with anionic and cationic substrates and with nonionic substrates, such as household soils, dirt, stains and the like. Household soil and dirt particulates may be composed of metals that do not ionize in aqueous solution including iron oxide, yttrium oxide, zinc oxide and the like. Although these particulates are non-polar, insoluble in water, and do not ionize in aqueous solution they do contain partial negative charges at regions of the molecule (at the metal and oxygen atoms). The antiredeposition agents of the present invention, such as PVP, generally contain a partial positive charge along the backbone of the polymer, such as $N^+$ in PVP, where an ionic bond forms resulting in dispersion in aqueous solution.

The compositions of the present invention are effective at a pH range of from about 5.0 to about 12.0, and pH modifying compounds, referred to herein as pH modifiers, are used to bring the pH of the composition within this pH range, and to maintain the pH within that range. pH modifiers comprise a compound capable of altering the pH of the composition to between about pH 5.0 and pH 12.0. An example of such a pH modifier is an alkali counter ion, in which alkali is understood to mean having base-like qualities, or is basic, and is related to OH— from the neutralization reaction of $H^+ + OH^- \rightarrow H_2O$, and may be the counter ion to the following ions, sodium ions ($Na^+$), potassium ions ($K^+$), calcium ions ($Ca^{+2}$), magnesium ions ($Mg^{+2}$), ammonium ($NH_4^+$) and amine ions ($NH_3^+$), for example, from ammonium hydroxide, isopropylamines, and alkanolamines), and the like. Other pH modifying compounds include known acids and bases, and buffering compounds useful for altering or maintaining a desired pH or pH range. The pH modifying compounds used in the compositions must be compatible with other components of the compositions, and pass standard screening for cleaning efficacy, challenge testing and storage stability.

Suitable chelating agents include compounds such as ethylenediaminetetraacetic acid; diethylenediaminepentaacetic acid; nitrilotriacetic acid; hydroxyethylenediaminetriacetic acid; iminodisuccinic acid; aminotrismethylenephosphonic acid; hexamethylenediaminetetramethylenephosphonic acid; diethylenetriaminepentamethylene-phosphonic acid, combinations and mixtures and the like. Water soluble chelating agents are useful in aqueous solutions or compounds that are sufficiently soluble at the volumes and pH of the composition.

Concerning suitable fragrances or fragrance materials for use in the surfactant-free cleaning compositions of the present invention, it should be noted that any desirable known scenting or fragrance types may be employed to produce such compositions provided that the fragrance or scent passes standard screening for cleaning efficacy, challenge testing and storage stability and, furthermore, that users/customers would be satisfied with the aesthetics (i.e., color, smell and the like) of cleaning composition containing the fragrance. Examples of suitable fragrances or fragrance materials for use herein include, but are not limited to, terpene compounds such as monocyclic terpenes such as limonene; dicyclic terpenes such as pinene; and acyclic terpenes such as myrcene and the like. Also, oxygenated terpene derivatives such as alcohols, aldehydes, esters, ethers, ketones and the like; as well as oxygenated aromatic derivatives such as alcohols, aldehydes, esters, ethers, ketones and the like may be employed as the fragrance material in the present compositions.

Exemplary of terpene compounds for use herein are oils derived from citrus peels such as lemons, oranges, limes, tangerines, grapefruits and the like. Such oils are comprised of about 70–90% (by weight) terpenes (limonene, pinene, and myrcene) with smaller amounts of alcohols (terpineol, linalool, geraniol, octanol, and nonanol) and aldehydes (citral and citronellal). Examples of an oxygenated terpene derivative suitable for use as a fragrance in the compositions of this invention are oils of eucalyptus globulus, which are comprised of about 80% (by weight) terpene ether (cineol) with smaller amounts of other terpene compounds. An example of an oxygenated aromatic derivative would be oil of wintergreen, which is comprised of about 98% (by weight) aromatic ester (methyl salicylate).

Suitable stabilizing agents, which also function as fragrance stabilizing agents, include a variety of solvents including, but not limited to, alcohols such as methyl alcohol, ethyl alcohol, isopropyl alcohol, propyl alcohol and the like; glycol ethers (including methyl, ethyl, propyl, isopropyl, butyl, phenyl, and ethylhexyl ethers) and glycol ether esters of glycols (such as ethylene glycol, diethylene glycol, triethylene glycol, propylene glycol, dipropylene glycol, tripropylene glycol and the like) including diethylene glycol monobutylether and diethylene glycol monobutylether acetate and mixtures thereof.

As with fragrance materials for use herein, any desirable known preservative may be employed to produce the compositions of this invention provided that the preservative passes standard screening for challenge testing and storage stability and, furthermore, that users would be satisfied with the aesthetics (i.e., color, smell and the like) of cleaning composition containing the preservative. Additionally, there are US regulations, such as EPA directions for use, that may have to be complied with when preservatives are added to the composition. Sufficient amounts of preservatives are those that meet standard screening for challenge testing and storage stability, and may also include amounts complying with EPA directions for use. Suitable preservative agents for use in the present invention include a variety of chemical compounds with the ability to impart to chemical formulas a resistance to microbial contamination in order to assure product safety and integrity over the useful life of the product. Such preservative agents include 1,3-dihydroxymethyl-5-5-dimethylhydantoin (DMDM Hydantoin); 1,2-benzisothiazolin-3-one; 5-chloro-2-methyl-4-isothiazolin-3-one; 2-methyl-4-isothiazolin-3-one; 3-iodo-2-propynyl butyl carbamate; phenoxyethanol; 2-bromo-2-nitropropane-1,3-diol; methyl paraben; propyl paraben; isopropyl paraben; butyl paraben; isobutyl paraben; diazolidinyl urea and hydroxymethylglycinate and mixtures thereof.

Generally, in formulating aqueous, surfactant-free cleaning compositions of the present invention, the following ranges of ingredients (as weight percentages per total weight of aqueous cleaning composition) may satisfactorily be used:

TABLE 2

Formulation ranges

| Ingredient | Operating Range | Preferred Range |
|---|---|---|
| dispersing agent | 0.01–10.0% | 0.05–1.0% |
| anti-redeposition agent | 0.001–10.0% | 0.05–1.0% |
| chelating agent | 0.01–5.0% | 0.05–1.0% |
| pH modifier | Quantity sufficient to adjust pH to about 5.0–12.0 | Quantity sufficient to adjust pH to about 9.0–10.0 |
| fragrance | 0.0000–2.0% | 0.0000–0.20% |
| stabilizing agent* | 0.05–25.0% | 0.1–2.0% |
| preservative agent | Sufficient amount | Sufficient amount |
| Water | Quantity sufficient to adjust weight percentage to 100% | Quantity sufficient to adjust weight percentage to 100% |

*A stabilizing agent also functions as a fragrance solubilizing agent when fragrance is present in the composition.

Operating range refers to amounts in compositions that are effective in the methods of the present invention.

Surfactant-free, aqueous cleaning compositions comprising the above ranges of components may be prepared from preformed concentrated stock solutions. In practice, these concentrated stock solutions are intended to be diluted with water by an end user at the site of application of the cleaning composition to a desired level depending on the particular soil extraction device or technique to be employed by the end user to treat the fiber surface. The concentrated stock solutions contain predetermined quantities (on a weight basis) of the desired ingredients so that upon dilution the resulting aqueous compositions will contain such ingredients in quantities (on a weight percent basis) corresponding to the above tabulated operating and/or preferred ranges of ingredients to be incorporated in the aqueous cleaning compositions. The concentrated stock solutions are normally diluted by a factor of from about 1:2 to about 1:256 to produce the aqueous composition for application to carpets, upholstery and other fibers and surfaces. Preferably, the concentrated stock solutions are diluted by a factor of from about 1:4 to about 1:128 and, most preferably, from about 1:16 to about 1:64.

An aspect of the present invention comprises a surfactant-free, aqueous cleaning composition comprising one or more polymeric dispersing agents, one or more polymeric anti-redeposition agents and a sufficient amount of a pH modifier to maintain the pH of the aqueous composition in a range of about pH 5.0 to about pH 12.0, or about pH 9.0 to about pH 10.0. In the present compositions, the absence of micelle-forming surfactants are used in methods for dispersion of particulate matter and preventing the redeposition of such particulate matter on fibers and other surfaces. An exemplary composition comprises the following ingredients:

a) one or more chelating agents, such as ethylenediaminetetraacetic acid;

b) one or more dispersing agents, such as polyacrylic acids;

c) one or more anti-redeposition agents such as polyvinylpyrrolidone;

d) a sufficient amount of pH modifiers, such as the counterions of sodium (Na), potassium (K), or ammonium, such as ammonium hydroxide ($NH_4OH$), isopropylamine and alkanolamines to maintain the pH of the composition in a range of about pH 5.0 to about 12.0; or in a range of about 9.0–10.0; and e) one or more stabilizing agents, such as an alcohol, for example, ethanol, or glycol ethers.

Optionally, a composition may further comprise a fragrance, such as a terpene or a terpene derivatives, and/or one or more preservatives, such as DMDM Hydantoin.

The compositions of the present invention are generally used as liquid aqueous solutions comprising at least one dispersing agent, at least one anti-redeposition agent, at least one pH modifier, at least one chelating agent, and at least one stabilizing agent, generally in methods of cleaning fibers and surfaces. Where used in liquid aqueous solutions, the ingredients of the composition are generally water soluble, or are sufficiently soluble in the volumes used or at the pH of the composition. Such compositions may further comprise other ingredients such as at least one fragrance or at least one preservative. Alternatively, the compositions of the present invention may be a dry powder that is admixed with water or other aqueous solutions to form an aqueous solution composition of the present invention. Such powders may comprise at least one dispersing agent, at least one anti-redeposition agent, and at least one chelating agent, and may optionally comprise at least one pH modifier, at least one stabilizing agent, at least one fragrance or at least one preservative. Such powders comprise dry ingredients that may be added as one or more individual powder ingredients to form a powder composition that when added to water may have further ingredients added, such as adjusting the pH with a pH modifier or adding a stabilizing agent to the liquid composition. Formulation of powder compositions are known in the art, and may further comprise additives needed for powder characteristics such as to keep the powder free flowing. Alternatively, the compositions of the present invention may also be found in paste or gel compositions comprising at least one dispersing agent, at least one anti-redeposition agent, at least one pH modifier, at least on chelating agent, and may further comprise at least one stabilizing agent, at least one fragrance or at least one preservative. Such paste or gel formulations are known, and additives needed for paste or gel formulations may be added to the compositions of the present invention.

Though not wishing to be bound by any particular theory, it is currently believed that the polymeric dispersing agents the present surfactant-free cleaning compositions take advantage of the lower energy of the fiber surface to force the particles off the surface and into the dispersing agent.

The aqueous compositions of the present invention provide surface tensions of greater than about 38 dynes/centimeter (cm) for application onto low energy fiber surfaces, which are generally less than about 35 dynes/cm, thereby establishing an energy barrier which is employed to maintain separation between the surface of the fiber and the surfactant-free cleaning composition. The formation of this energy barrier allows for the efficient transfer of particulate matter, including particles and dyes, from the surface of a fiber into an aqueous liquid phase, enables the dissolution or dispersion of charged particles, such as dirt and acid dye, polar soils, such as sugars and starches, and non-polar soils, such as oil, from the surface of the fiber into the cleaning compositions of this invention. The energy barrier formed between a fiber surface and the compositions of the present invention prevent redeposition of particulate matter and dye particles onto a fiber and facilitate adsorption of the dispersed particles into a clean cloth used to remove the unwanted soil, or transport the particulate matter away with the removal of the solution, and eliminate or reduce the amount of residual cleaning solution left on the fiber after completion of the cleaning task when compared to the residual amounts remaining after cleaning with surfactant containing solutions.

It should be noted that the advantages achieved by employing the higher surface tension cleaners of the present invention, while being most pronounced on fibers with a soil-repellant finish, are also realized to a lesser degree on non-treated synthetic fibers (i.e., nylon, polyester, polypropylene and acrylic), which are intrinsically low energy surfaces and essentially non-absorbent to water based liquids.

The present invention comprises surfactant-free cleaning compositions having a surface tension of at least about 38 dynes/cm, or above 60 dynes/cm that is applied to a fiber, or fiber surface such as carpets, upholstery and the like. Compositions with surfactants, which lower surface tensions, are known to penetrate the typical topical hydrophobic fluorochemical soil repellant and/or stain resistant finish treatments on the fiber surface. The compositions of the present invention may be applied to a stained or soiled area employing a hand held sprayer, a pull/push applicator, a woven or non-woven fabric wipe or a similar device. The application of the compositions of the present invention to the fiber or fiber surfaces or other surfaces may be applied with any range of force to contact the composition with the fiber or surface, or to remove the composition from the fiber or surface. The amount of force used in application of composition has effects on the movement of the particulate matter and dye particles. For example, in the case of spots and stains, such as red Kool-Aid, forceful application of compositions may cause penetration of the stain into the fiber which causes increased potential for staining. Penetration into carpet backing causes the stain to seem to disappear, only to re-migrate to the surface during the drying stage. In the case of application force of the compositions to remove particulate matter, if the soil can be dispersed without being forced deeper in the carpet, the efficacy of the extraction equipment is enhanced, and there is less work needed to remove the particulate matter. If a lower force is used to disperse the particulate matter, there is a lower amount of liquid that reaches deeper into the fabric or carpet. If liquid containing dispersed particulate matter is forced more deeply into the fabric, it will require more force to remove that liquid, which is not an issue with extraction systems that have high force for extraction, such as truck mounted or industrial cleaners. Less forceful extraction systems, such a handheld, or home carpet or upholstery cleaning machines function at a greater efficiency using the compositions of the present invention. The handheld or home machine has lower force application, the composition is effective at dispersing the particulate matter, and the lower removal force of the handheld or home machine can still remove the particulate matter effectively.

The methods of the present invention may be used with hand cleaning, or using machines such as a hand-held, upright, truck mount, or commercial extraction devices. Such methods are normally performed by incorporating a suitable concentrated solution of the cleaning composition into an applicator and diluting the concentrate sufficiently to enable the diluted cleaning composition to perform the cleaning function satisfactorily when applied to a fiber surface. In operation, the benefits of a surfactant-free formulation are realized since cleaning compositions that do not penetrate the fiber not only provide better stain and soil cleaning benefits on the fiber surface, but also are more readily extracted by extraction devices. The surfactant-free compositions of the present invention with higher surface tension characteristics than surfactant containing cleaning compositions are applied to a fiber or surface and any soiled or stained areas that are contained on the surface are then available for removal from the surface by known absorption or extraction techniques.

Literature has discussed the anti-redeposition agent interaction with surfactants. This interaction is used to benefit surfactant micelle properties. At high surfactant to anti-redeposition agent ratios, the anti-redeposition polymer enters the surfactant micelle, reducing critical micelle concentration and promoting rod-like micelle formation, enhancing performance of the surfactant properties. However, at high anti-redeposition agent to surfactant ratios, it is theorized that this interaction is a hindrance to anti-redeposition properties due to attachment of surfactant monomers to the anti-redeposition agent polymer reaction sites. As a result, the dispersion forces are neutralized, and particulates are not dispersed into the aqueous solutions.

The mechanism of fiber cleaning, the interaction with surfactants and dyes, and the suspension of particulates has indicated that these anti-redeposition agent interactions relate to dipole-dipole, dipole-polarizable, and electron charge attraction forces of the anti-redeposition agent polymeric molecule. The anti-redeposition agent molecule has strongly negative oxygen atoms with a strong affinity for cations Anti-redeposition agents, when properly selected, aid the dispersing agent in separating particles by providing additional steric repulsion forces. Thus, the present invention comprises compositions with improved removal of metal-associated soils from fibers, such as carpets and upholstery containing transition metals chosen for particle size and chemical characteristics naturally occurring in soil. Conversely, surfactant monomers hinder this function and lead to bridging flocculation in which the anti-redeposition and dispersing agents pull the particles together to make larger particles or even bridging the particles to the surface being cleaned, thus attaching the particulates to the fibers.

Residual surfactants and hydrophobically modified polymers present on carpet and upholstery interfere with the dispersion forces of the compositions of the present invention until residual surfactants are removed during the cleaning process. When particulate are effectively dispersed and suspended in an aqueous solution without first applying a carpet and upholstery cleaning composition that causes the soil and particulate to penetrate deep into the fabric, such as a surfactant containing composition, the particulates are more efficiently removed due to improved particulate suspending activity coupled with improved extraction solution recovery rates. The functional advantages of the compositions of the present invention are best seen when residual surfactant removal has occurred, or surfactants were never applied. A surfactant-containing cleaner may be required to remove oil and grease residue.

Methods of the present invention comprise cleaning one or more surfaces comprising fibers by applying a composition taught herein to the fibers or surfaces, which removes particulates and prevents the redeposition of the particulates, such as metal-associated soils or allergens. By removing the particulates from the indoor environment, there is less particulate matter the air. With less particulate matter in the air, humans or animals are exposed to fewer particulates with the attendant health benefits of cleaner air. Methods of treating or preventing allergic reactions comprise applying a composition taught herein to a fiber, a surface comprising fibers, or other surface, allowing a sufficient amount of time to remove particulates and allergens associated with the fibers, and removing the composition comprising the particulates, thus preventing such particulates from redepositing on the fiber, a surface comprising fibers, or other surface. Methods of treating or preventing inflammatory responses or cardiac-related conditions in humans and animals comprise applying a composition taught herein to fiber, a surface comprising fibers, or other surface, allowing a sufficient amount of time to remove particulates associated with the fibers, and removing the composition comprising the particulates, thus preventing particulates from redepositing on the surface comprising fibers, and lowering the overall particulate load in the environment, and concomitantly, reducing exposure of the humans or animals to the particulates and lessening the pathological responses in the humans or animals to the particulates. Methods of affecting indoor air quality comprise applying a composition taught herein fiber, a surface comprising fibers, or other surface, allowing a sufficient amount of time to remove particulates associated with the fibers, and removing the composition comprising the particulates, thus preventing particulates from redepositing on the surface comprising fibers, and lowering the overall particulate load in the environment In preventing redeposition of the particulate matter, the particulates are removed from the environment.

The present invention comprises methods and compositions for removing particulates from fibers and surfaces. The compositions comprise aqueous solutions comprising at least one dispersing agent; at least one anti-redeposition agent; at least one pH modifier; at least one chelating agent; at least one stabilizing agent; and; and optionally, a fragrance and/or at least one preservative agent. Water soluble compounds are useful in aqueous solutions or compounds that are sufficiently soluble at the volumes and pH of the composition. Methods of the present invention comprise applying a composition to a fiber or surface, or contacting a fiber or surface with a composition, allowing the composition to remain in contact with the fiber or surface so that at least some portion of the particulates present in, on or adjacent to the fiber or surface are dispersed in the composition, and removing the composition from contact with the fiber or surface. The methods comprise methods for removing particulates from fibers or surfaces, whether the fibers and surfaces are found in interior environments or exterior environments, which generally means an environment inside an enclosed structure or outside of a structure, respectively. Methods comprise removing particulates from fibers or surfaces, removing allergens from fibers or surfaces, methods for improving indoor air quality, methods for treating allergic or inflammatory conditions in humans or animals by removing the particulates or allergens which may be causing or exacerbating the allergic or inflammatory conditions, from the environment, particularly an interior environment, and methods for preventing inflammatory reactions or allergic reactions in humans or animals by removing the particulates or allergens which may be causing or exacerbating the allergic or inflammatory conditions.

The methods used in these and other methods of removing particulates from fibers and surfaces may comprise multiple applications of the compositions or multiple contacting of the fibers or surfaces, so as to remove as much of the particulates as desired. The applying or contacting steps, along with each sequential removing of the composition steps may performed more than one time.

The compositions of the present invention may be provided in concentrated solutions that are then diluted to effective concentrations for application to the fibers or surfaces. The compositions generally comprise solutions of effective amounts of the ingredients described herein. The compositions may have a surface tension greater than about 38 dynes per centimeter. The compositions comprise at least one dispersing agent, which is polyacrylic acid, polyacrylic acid/maleic acid copolymers; styrene/maleic anhydride copolymers, polymethacrylic acid, polyaspartic acid or combinations or mixtures thereof. The compositions comprise at least one anti-redeposition agent which is polyvinylpyrrolidone; polyvinylbetaine; polyvinyl pyrrolidone/vinylacetate copolymers; polyvinylpyrrolidone/dimethylamino-ethylmethacrylate copolymers; polyvinylpyrrolidone/acrylic acid copolymers; polymethylvinylether/maleic anhydride copolymers; polyvinylpyridine-n-oxide or combinations or mixtures thereof. Water soluble compounds are useful in aqueous solutions or compounds that are sufficiently soluble at the volumes and pH of the composition. The compositions comprise at least one pH modifier which may be a counter ion of sodium ions, potassium ions, calcium ions, magnesium ions, ammonium ions or amine ions or combinations or mixtures thereof. The compositions at least one chelating agent is ethylenediaminetetraacetic acid; diethylenediaminepentaacetic acid; nitrilotriacetic acid; hydroxyethylene-diaminetriacetic acid; iminodisuccinic acid; aminotris-methylenephosphonic acid; hexamethylenediaminetetramethylenephosphonic acid; diethylenetriamine-pentamethylenephosphonic acid or combinations or mixtures thereof. Water soluble chelating agents are useful in aqueous solutions or compounds that are sufficiently soluble at the volumes and pH of the composition. The compositions comprise at least one stabilizing agent which is an alcohol, methyl alcohol, ethyl alcohol, isopropyl alcohol, propyl alcohol, glycol ether, methyl glycol ether, ethyl glycol ether, propyl glycol ether, isopropyl glycol ether, butyl glycol ether, phenyl glycol ether, ethylhexyl ether; glycol ether ester of glycols, ethylene glycol, diethylene glycol, triethylene glycol, propylene glycol, dipropylene glycol, tripropylene glycol, diethylene glycol monobutylether, diethylene glycol monobutylether acetate, or combinations or mixtures thereof.

The compositions may further comprise at least one preservative which is 1,3-dihydroxymethyl-5-5-dimethylhydantoin (DMDM Hydantoin); 1,2-benzisothiazolin-3-one; 5-chloro-2-methyl-4-isothiazolin-3-one; 2-methyl-4-isothiazolin-3-one; 3-iodo-2-propynyl butyl carbamate; phenoxyethanol; 2-bromo-2-nitropropane-1,3-diol; methyl paraben; propyl paraben; isopropyl paraben; butyl paraben; isobutyl paraben; diazolidinyl urea and hydroxymethylglycinate or combinations or mixtures thereof. Water soluble compounds are useful in aqueous solutions or compounds that are sufficiently soluble at the volumes and pH of the composition. The compositions may optionally comprise at least one fragrance, wherein the at least one fragrance is a terpene compound; monocyclic terpene; limonene; dicyclic terpene; pinene; acyclic terpene; myrcene; oxygenated alcohol, aldehyde, ester, ether or ketone terpene derivative; oxygenated alcohol, aldehyde, ester, ether or ketone aromatic derivative; oil derived from citrus peel; lemon oil, orange oil, lime oil, tangerine oil, grapefruit oil; oils of eucalyptus globulus, oil of wintergreen, or combinations or mixtures thereof. The pH of the solution compositions of the present invention are effective in a pH range of about 5.0 to about 12.0, which is accomplished by the pH modifier.

For example, a method for removing allergens, comprises contacting interior environment fibers or surfaces with a composition comprising, at least one dispersing agent; at least one anti-redeposition agent; at least one pH modifier; at least one chelating agent; at least one stabilizing agent; and may further comprise at least one preservative agent; and removing a portion of the composition from the contacted interior environment fibers or surfaces after a time sufficient to disperse at least some portion of the total amount of particulate matter. Water soluble compounds are useful in aqueous solutions or compounds that are sufficiently soluble at the volumes and pH of the composition. When an aqueous or liquid composition, the composition has a surface tension of greater than about 38 dynes per centimeter. The composition may further comprise at least one fragrance. An example of such a particulate dispersing composition, comprises at least one dispersing agent; at least one anti-redeposition agent; at least one pH modifier; at least one chelating agent; and at least one stabilizing agent. The composition may further comprise at least one preservative agent or at least one fragrance, or both. Such a particulate dispersing composition may comprise, in weight percentages per total weight of the composition, 0.01–10.0% total amount of dispersing agent; 0.001–5.0% total amount of anti-redeposition agent; sufficient pH modifier to adjust the pH of the composition to a pH of about 5.0–12.0; 0.01–10.0% total amount of chelating agent; 0.0–2.0% total amount of fragrance; 0.05–25.0% total amount of stabilizing agent; sufficient amount of at least one preservative agent; and sufficient water to adjust the weight percent of the aqueous composition to 100%.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

A 1200 gram (g) sample of a surfactant-free aqueous cleaning composition in accordance with the present invention was prepared by blending, in laboratory scale apparatus, the following ingredients:

TABLE 3

A Cleaning Composition

| Ingredients | Weight Percent (%) | Grams (g) |
|---|---|---|
| Water (Tap) | 80.776 | 969.312 |
| Sodium iminodisuccinate (34%*) | 9.800 | 117.6 |
| Polyacrylic acid, sodium salt (50%) | 2.404 | 28.848 |
| Polyvinylpyrrolidone (30%) | 6.670 | 80.04 |
| DMDM Hydantoin | 0.0500 | 0.6 |
| Ethyl Alcohol | 0.3000 | 3.6 |
| Totals | 100.0000 | 1200.00 |

*A 34% aqueous solution of sodium iminodisuccinate, of which 117.6 g was added to the cleaning composition.

The mixing procedure employed in producing the 1200 g sample included initially weighing and incorporating 969.312 g water into a 5000 mL polypropylene beaker and then placing the beaker containing the water on a steel mixer base, inserting a Talboy agitator into the beaker and initiating agitation. Then, 117.6 g Sodium iminodisuccinate, 28.848 g polyacrylic acid (sodium salt), 2.50 g polyvinylprrolidone, a preservative (MDM Hydantoin) and 3.6 g ethyl alcohol were incorporated, in listed order, into the water under agitation. The combined mixture was then blended for 10 minutes after which an 8-ounce (oz) portion of the 2500 mL sample mixture was collected and transferred for Quality Control (QC) testing. Other portions of the mixture were collected diluted as suitable for use as Test Samples for the performance testing detailed hereinafter in Examples 2, 3 and 4.

The QC testing of the 8-ounce sample resulted in the following data:

TABLE 4

Quality Control

| Property | Predetermined Ranges | Test Results |
|---|---|---|
| Appearance/Odor | — | Clear, pale colored liquid with bland odor |
| pH | 8.5–9.0 | 8.75 |
| Sp. Gravity @ 25° C. | 1.035–1.045 | 1.04 |
| % Solids | 7.0–7.5% | 7.25 |
| Surface Tension | >60 dynes/cm | 63.4 |

Example 2

Several acrylic copolymers are described in U.S. Pat. No. 6,835,704 for use as dispersing and/or anti-redeposition agents, and the selection of an appropriate acrylic copolymer depends on properties including wetting (surface tension reduction), foaming (polar attraction disruption and film viscosity increase), and anti-redeposition agent interaction. Pemulen® 1622 Polymeric Emulsifier type acrylic acid polymer is one example. Pemulen 1622 is hydrophobically modified by addition of C10–30 alkyl acrylate monomer to the acrylic acid polymer backbone. It is believed the molecule imparts undesirable surfactant-like properties to the formulation.

Pemulen® 1622 Polymeric Emulsifier was incorporated into the base formulation (as described in Example 1) at a concentration of 1.6% Pemulen 1622. Both formulations were diluted 1:16 with tap water.

Table 5 summarizes the properties and results, followed by detailed discussion and observations.

TABLE 5

Effects of Hydrophobically Modified Polymer

| Properties | Example 1 Formula | Example 1 Formula (plus 1.6% Pemulen 1622) |
|---|---|---|
| Surface Tension | 63.4 dyne/cm | 69.8 dyne/cm |
| Foaming[1] | <5 mL | 125 mL |
| Viscosity[2] | 0 cps | 8 cps |
| Soil Dispersion Test (60 Minute) | 3.0 | 0.5 |

[1] Modified Ross-Miles (5 Minute Foam)
[2] Brookfield LV Viscometer/Spindle 1 at 30 rpm
[3] To simulate the use of the surfactant-free aqueous cleaning compositions of the present invention to disperse common dirt and to demonstrate the improved dispersion achieved with the compositions of the present invention as compared withprior art commercial products, a 16 g test sample of an aqueous dilution (1:16) of the cleaning composition produced in Example 1 was introduced into a 22 mL KIMAX Sample Vial (Fisher Cat # 03-339-25F) along with a dirt sample comprising 0.2 gGeorgia Red Clay which was obtained from a household yard and was prepared by air drying at 23° C. and 70% relative humidity and, then, grinding with a mortar and pestle. After the test sample and the control sample cleaning solutions and the dirtsample were introduced into the Sample Vials, the Sample Vials were each capped and held without shaking for 15 seconds. Then, each of the Sample Vials was inverted three times, followed by a 60 second holding period without shaking andthen each of the Sample Vials was again inverted three times. Based on visual observations, the dispersion rate of the dirt in each of the tested cleaning solutions was determined and recorded after a 1 minute, a 15 minutes and a 60 minutes intervaland tabulated.

The micelle-forming surfactants which have been utilized in prior art cleaning compositions have functioned to reduce the water/oil interfacial tension at the surface of the fiber substrate for purposes of encapsulating oil particles for removal in much the same manner as is typical for most consumer cleaning products such as hard surface cleaners, fabric cleaners, personal care products and the like. This lowering of the surface tension (i.e., the force per unit length on the surface that opposes the expansion of the surface area) when prior art aqueous cleaning solutions have been utilized have been found to be counterproductive in practice resulting in the cleaning solution causing many soils and/or stains to penetrate into and "wet" the fiber surface, thereby, to cause the soiled section or stain in the fiber surface to spread over a larger area rather than to be removed. Additionally, this "wetting" tends to cause fibers to untwist, particularly under mechanical force, thereby causing increased fiber damage and wear.

Testing indicates that Pemulen 1622 does not reduce surface tension. The slight increase in surface tension observed is likely related to the increase in viscosity. Consequently, the Pemulen Polymeric Emulsifier does not hinder the invention with regard to problems associated with wetting, such as spreading of stains or fiber untwisting.

The polymer cannot reduce surface tension because the polymer does not form typical surfactant micelle structures in aqueous solution. As anticipated, incorporation of an hydrophobically modified polymer into the base formulation has a significant effect on foam and foam stability. This foam is the result of forces other than those typically associated with surfactant micelles. Molecules that incorporate both polar and non-polar units may be either soluble or dispersed in water and capable of breaking the high-energy polar forces that cause bubbles to break. Surfactants are known for the ability to break these forces at very low concentrations due to the formation on micelles. Once these polar forces are broken, foam occurs. Pemulen Polymeric Emulsifiers exert a similar surfactant-like ability by incorporation of both polar and non-polar units. Once foam is formed, its stability is dependent on several film properties including film thickness, drainage, viscosity, elasticity, permeability and the presence of electrical double layers.

Of the mechanisms affecting film rupture, the initial concern is liquid drainage out of the film. Hence, the hydrodynamic flow properties within the film (surface viscosity and film elasticity) come into play. As the film thickness thins, increased surface viscosity and film elasticity properties tend to help resist localized thinning of the film, which causes film rupture.

From Table 5, both the foam and viscosity measurements appear to support the theory that hydrophobically modified polymers influence these non-micelle forces (film thickness, drainage, viscosity, elasticity, and possibly permeability), which are likely the reasons for foam formation and foam stability. However, while foam is undesirable from a marketing point of view (since it makes it more difficult to sell the product as "surfactant free"), this alone is not reason enough to discount Pemulen Polymeric Emulsifiers from use in the invention since the effect the polymeric dispersion, dissolution and redeposition of charged particles in manner very similar to surfactants as described in U.S. Pat. No. 6,835,704.

From Table 5, it is noted that the soil dispersion testing indicates that the Pemulen Polymeric Emulsifier interferes with the anti-redeposition agent, thereby inhibiting the composition's ability to prevent the redeposition of soil and to facilitate the quicker absorption of soil.

Example 3

To measure the effect of surfactant-containing cleaners on drying times, the base formulation (as described in Example 1) was applied under standard lab conditions of 23° C. @ 40–60% relative humidity. Each carpet cleaning composition was diluted to the maximum recommended extraction solution dilution ratio and sprayed onto an approximately 9"×9" area of EverSet® Commercial carpet (Style No. DC 038, Ultron Nylon 6,6) at an application rate of 0.25 grams per inch$^2$ (20 gram) with a hand held spray/stream sprayer adjusted to a medium spray pattern. After 60 seconds, a three-pass vacuum extraction was applied using a Bissell Little Green Machine®. The drying period was initiated after first measuring the amount of cleaning solution removed by vacuum extraction.

TABLE 6

Effect of Surfactant-Containing Cleaner on Drying Times

| | Carpet Cleaning Composition Extraction Solutions | | |
|---|---|---|---|
| Time | Water (Control) | Example 1 Composition (1:16) | Extraction SC* (1:320) |
| 0.00 | 74.35% | 76.92% | 56.14% |
| 0.50 | 81.20% | 83.70% | 63.22% |
| 1.25 | 90.90% | 92.03% | 71.83% |
| 2.00 | 95.40% | 95.99% | 79.01% |
| 3.00 | 97.35% | 98.03% | 85.40% |
| 4.00 | 99.25% | 99.21% | 90.15% |
| 5.25 | 100.00% | 100.00% | 93.60% |
| 6.50 | 100.00% | 100.00% | 95.79% |
| 8.00 | 100.00% | 100.00% | 98.00% |

*Surfactant containing composition

The present invention compositions (even at the highest recommended dilution) had an extraction solution recovery rate and drying profile equal to water. Drying time (dry to the touch) was reduced from 6 hours to 2 hours as compared to a typical surfactant containing cleaner (i.e. Extraction SC from Johnson Wax Professional), a 50–70% reduction in drying time vs. the surfactant containing system.

TABLE 7

Surface Tension Measurements

| Properties | Water | Example 1 Formula | Extraction SC |
|---|---|---|---|
| Dilution Ratio | NA | 1:16 | 1:320 |
| Surface Tension | 72.1 dyne/cm | 63.4 dyne/cm | 34.0 dyne/cm |

TABLE 8

Surface Tension Properties

| Surface Tension | Properties |
|---|---|
| Less than 40 dynes/cm | Fast-moderate wetting. Increased soil penetration into carpet backing |
| 40–50 dynes/cm | Slow wetting. Slightly increased soil penetration into carpet backing. |
| >60 dynes/cm | Very slow wetting. Decreased soil penetration into carpet backing |

Example 4

The results of the cleaning efficacy data were obtained by X-ray fluorescence (XRF). Data generated in accordance with PTL (DRAFT)—Standard Test Practice Using X-Ray Fluorescence for Evaluating Cleaning Effectiveness of Carpet Cleaning Processes (2004) supported the claims described herein of improved compositions and processes to remove metal-associated soils from carpets.

The test soil used a standard set of compounds containing elements suitable for XRF detection, chosen for particle size, hardness and surface characteristics of naturally occurring soils commonly found in household carpet soil (such as clay and sand).

TABLE 9

Test Soil Characteristics

| Compound | Particle Size | Comments |
|---|---|---|
| Iron Oxide | <1 μm | Commonly found in soil |
| Zinc Oxide | <74 μm | Clay-like consistency |
| Yttrium Oxide | <10 μm | Sand-like characteristics |
| Zirconium Boride | <44 μm | Black dust-like characteristics |

The test soil was first applied to Zytel™ 01FNC010 nylon pellets, which were used to transfer the test soil to carpet test specimens following ASTM D6540. The carpet test specimens (untreated1 or precleaned2) were mounted securely inside a rotating drum with the pile surface exposed and subjected to an accelerated soiling process. The degree of soiling (a) was assessed by XRF analysis to determine the starting concentration of each compound. The carpet test specimens were pre-sprayed (1 gallon use solution per 200 ft$^2$. After 15 minutes, the samples were cleaned by two extraction strokes and two dry strokes starting at the bottom of the sample on the first stroke at 1.0 foot per second for a total of four strokes. The carpet test specimens were allowed to dry for 24 hours and the soil removal (b) was assessed by XRF analysis. The % soil removal was determined using the following formula:

$$\% \text{ Soil removal} = a-b/a(100)$$

TABLE 10

% Soil Removal (In-tank Commercial[3] Extraction)

| | | Process Dilutions | | | % Removal | | | |
|---|---|---|---|---|---|---|---|---|
| | Cleaning Composition | Pre-Spray | Extraction | Carpet Surface | $Fe_2O_3$ | $Y_2O_3$ | ZnO | Total |
| 1 | Example 1 | 1:16 | 1:64 | Unt[1] | 101 | 98 | 99 | 99 |
| | | | | Precl[2] | 94 | 93 | 93 | 93 |
| 2 | Example 1 | 1:64 | 1:64 | Unt[1] | 97 | 95 | 94 | 95 |
| | | | | Precl[2] | 88 | 91 | 89 | 89 |
| 3 | Extraction SC | 1:320 | 1:320 | Unt[1] | 90 | 91 | 90 | 90 |
| | | | | Precl[2] | 88 | 90 | 89 | 89 |

TABLE 11

% Soil Removal (In-tank Household[4] Extraction)

| | | Process Dilutions | | | % Removal | | | |
|---|---|---|---|---|---|---|---|---|
| | Cleaning Composition | Pre-Spray | Extraction | Carpet Surface | $Fe_2O_3$ | $Y_2O_3$ | ZnO | Total |
| 1 | Example 1 | 1:16 | 1:64 | Unt[1] | 58 | 56 | 56 | 57 |
| | | | | Precl[2] | 54 | 53 | 53 | 53 |
| 2 | Example 1 | 1:64 | 1:64 | Untr[1] | 57 | 55 | 55 | 55 |
| | | | | Precl[2] | 52 | 50 | 50 | 50 |
| 3 | Bissell | 1:64 | 1:64 | Unt[1] | 42 | 41 | 40 | 41 |
| | | | | Precl[2] | 38 | 37 | 37 | 37 |

TABLE 12

% Soil Removal (In-tank Household[5] Extraction)

| | | Process Dilutions* | | | % Removal | | | |
|---|---|---|---|---|---|---|---|---|
| | Cleaning Composition | Pre-Spray | Extraction | Carpet Surface | $Fe_2O_3$ | $Y_2O_3$ | ZnO | Total |
| 1 | Example 1 | 1:16 | 1:64 | Unt[1] | 62 | 60 | 59 | 60 |
| | | | | Precl[2] | 58 | 56 | 56 | 56 |
| 2 | Example 1 | 1:64 | 1:64 | Unt[1] | 60 | 58 | 58 | 58 |
| | | | | Precl[2] | 54 | 52 | 52 | 53 |
| 3 | Hoover | 1:64 | 1:64 | Unt[1] | 44 | 43 | 43 | 43 |
| | | | | Precl[2] | 40 | 39 | 40 | 40 |

[1]Untreated Carpet Surface - Mohawk Spotlite (Style 25418-121), 25-oz/square yd, Pile 0.470" cut Nylon
[2]Treated Carpet Surface - Mohawk Spotlight precleaned with 0.1% Magnesium lauryl sulfate and dried 48 hours at 25° C.
[3] Commercial Truck Mount - ProChem Performer Model 980060
[4]Household Unit - Bissell Proheat Model 8910
[5]Household Unit - Hoover SteamVac Model F5900-900
*Dilutions of the composition of Example 1.

In operation, the benefits of a surfactant-free formulation were realized since cleaning compositions that do not penetrate the fiber not only provide better stain and soil cleaning benefits on the fiber surface, but also are more readily extracted by extraction devices. Functionally, the absence of surfactants in the compositions of the present invention greatly enhanced the effectiveness of these cleaning compositions as compared with prior art surfactant containing cleaning compositions since the presence of surfactants in the prior art products reduced the surface tension of the cleaning composition and significantly reduced the dispersing properties of the composition. In this regard, the surfactant-free compositions of the present invention were formulated to exhibit higher surface tension characteristics than prior art cleaning compositions when applied to a fiber surface whereby any soiled or stained areas are contained on the surface and are available for subsequent removal from the surface by known absorption or extraction techniques."

The data described herein showed that compositions of the present invention removed metal-associated soils from carpets more efficiently than prior art surfactant-containing cleaning compositions. Generally, the process dilutions were very near economical equivalents.

It appeared that the presence of residual surfactant on carpets previously cleaned with surfactant containing cleaning compositions may reduce the efficiency of the present invention. However, since surfactant chemistry may be used for certain greasy and oily residues, the most efficient process, may be to clean first by use of the present invention by extraction, followed by spot cleaning with a minimum quantity of surfactant based cleaner, with subsequent extraction with surfactant-free cleaning compositions as described in the present invention to reduce surfactant residues in the carpet to a minimum level.

The improved process of the present invention became more evident in household wet extraction equipment due to a less efficient vacuum design in household equipment. The significant performance improvement with household equipment (as compared to commercial equipment) is believed to be due to a combination of factors, the first of which is the improved exchange rate noted in the data presented in FIG. 1. Here it is noted that surfactant-containing solutions were more difficult to remove by vacuum extraction from carpeting.

Example 5

A 2500 gram (g) sample of a surfactant-free aqueous cleaning composition in accordance with the present invention was prepared by blending, in laboratory scale apparatus, the following ingredients:

TABLE 13

| Cleaning Composition | | |
|---|---|---|
| Ingredients | Weight Percent (%) | Grams (g) |
| Water (Tap) | 97.9670 | 2449.17 |
| EDTA, Tetrasodium salt | 1.2000 | 30.00 |
| Polyacrylic acid, sodium salt | 0.3800 | 9.50 |
| Polyvinylpyrrolidone | 0.1000 | 2.50 |
| DMDM Hydantoin | 0.0500 | 1.25 |
| Ethyl Alcohol | 0.3000 | 7.50 |
| #181335 Lemon | 0.0030 | 0.08 |
| Totals | 100.0000 | 2500.00 |

The mixing procedure employed in producing the 2500 g sample included initially weighing and incorporating 2449.17 g water into a 5000 mL polypropylene beaker and then placing the beaker containing the water on a steel mixer base, inserting a Talboy agitator into the beaker and initiating agitation. Then, 30.00 g EDTA (tetrasodium salt), 9.50 g polyacrylic acid (sodium salt), 2.50 g polyvinylpyrrolidone and a preservative (DMDM Hydantoin) were incorporated, in listed order, into the water under agitation. The resulting mixture was blended for 5 minutes. Separately, 7.50 g ethyl alcohol and 0.08 g fragrance (#181335 Lemon) were weighed and mixed in a 50 mL Pyrex beaker and this mixture was pre-blended with a spatula in the 50 mL beaker after which the resulting pre-blend was introduced into the original mixture in the 5000 mL polypropylene beaker. The combined mixture was then blended for 10 minutes after which an 8 ounce (oz) portion of the 2500 mL sample mixture was collected and transferred for Quality Control (QC) testing. Other portions of the mixture were collected and introduced into 32 oz. high density polyethylene (HDPE) containers with a suitable closure (28–400 High Flow Pull Push manufactured by Creative Packaging Corp. or a Model 0176 spray/stream/off trigger sprayer manufactured by Owens-Brockway) to be used as Test Samples for the performance testing detailed hereinafter in Examples 6 and 8.

The QC testing of the 8 ounce sample resulted in the following data:

TABLE 14

| Quality Control | | |
|---|---|---|
| Property | Predetermined Ranges | Test Results |
| Appearance/Odor | | Clear liquid/mild citrus odor |
| pH | 9.0–9.5 | 9.24 |
| Sp gravity at 25° C. | 0.7–0.8 | 0.76 |
| Surface tension | >60 dynes/cm | 63.4 dynes/cm |

Example 6

To simulate use of the surfactant-free aqueous cleaning compositions of the present invention for stain removal on stain-resistant carpeting and to demonstrate the improved stain removal results achieved with the compositions of the present invention as compared with prior art commercial products, Test Samples of the cleaning composition produced in Example 5, packaged in a 32 ounce container with a high flow pull/push applicator, were applied to a variety of laboratory staining agents and were blotted and the resulting stain ratings were compared with the stain rating results achieved employing various commercially available prior art cleaning compositions as Controls under the same test conditions.

For purposes of this comparative test, a series of 1 1/2" stains were applied to a test carpet at 2 1/2" intervals by pipette transfer of approximately 6 mL of various staining agents tabulated below onto the carpet surface. The stains were conditioned for 24 hours at 23. degree.C. (70% relative humidity) and excess stain was scraped from the surface with a scraper.

Then, a 7 g test sample of the cleaning composition produced in Example 5 was applied to each of the stained areas on the carpet surface using a high flow pull/push applicator. For purposes of providing control samples for comparative testing, two additional 7 g samples comprising two commercially available prior art cleaning products (i.e., one sample being prepared with RESOLVE®™ "Spot and Stain" and the other being prepared with BISSELL "Tough Stain Precleaner"™) were applied to in a similar manner to comparable stained areas on separate carpets. Three minutes after application, all of the stained areas were blotted with no more than two paper towels (as necessary). Then, additional 7 g test samples of each of the cleaning compositions were reapplied to the stained areas and these areas were again blotted until no further transfer of stain from the carpet to the towels was noted (about 10 minutes). If necessary, a scraper was employed to agitate any undissolved dried particles remaining on the carpets. A final 7 g Test Sample of each of the cleaning composition samples was reapplied to the stained areas and these areas were blotted again until no transfer was noted (about 5 minutes). Thereafter, the carpet was conditioned for 24 hours at 23° C. and the following tabulated comparative stain rating results were determined based on visual inspection of the carpet after treatment:

TABLE 15

Stain Rating Results

Cleaner Compositions

| Staining Agents | Test[A] | Control 1[B] | Control 2[C] |
|---|---|---|---|
| Grape Juice ("Welch's 100% Grape Juice) | 5.0 | 4.5 | 4.5 |
| "Kool-Aid" Cherry Burst, pre-sweetened, pre-mixed | 4.8 | 3.5 | 3.0 |
| Wine (Mogen David Concord) | 4.8 | 4.5 | 4.5 |
| Mustard (French's) | 3.5 | 3.5 | 3.0 |
| Chocolate Syrup (Hershey's Genuine | 5.0 | 4.8 | 4.8 |
| Ragu Brand (Meat Sauce) | 4.7 | 4.5 | 4.5 |

[A]Cleaning Compositions from Ex. 5
[B]Resolve ® "Spot and Stain"
[C]BISSELL "Tough Stain Precleaner" ™

Rating Scale:
5—no stain remaining
4—75% of stain removed
3—50% of stain removed
2—25% of stain removed
1—0% of stain removed Example 7

Typically, the surfactants employed in prior art cleaning compositions have been incorporated for purposes of lowering the surface tension of aqueous cleaning solutions when the surfactants are added at concentrations above critical micelle concentrations (CMC) of the surfactants.

In this Example, the surface tension characteristics of various conventional prior art cleaning compositions were measured in comparison with the surface tension exhibited by the cleaning compositions of the present invention. As determined by measurement with a calibrated CSC-DuNouy Tensiometer (Model 70535; SN 12516), the prior art cleaning compositions exhibited surface tensions below 35, and typically between 22 and 35 dynes/cm as compared with the cleaning compositions of the present invention which exhibit surface tensions of at least about 38.0 dynes/cm and higher as is demonstrated in the following Table 16.

TABLE 16

Surface Tension Measurements

| Carpet Cleaning Compositions | Dynes/cm |
|---|---|
| Resolve ® "Spot and Stain" | 22.0 |
| BISSELL "Tough Stain Precleaner" ™ | 33.2 |
| Formula 409 ® Carpet Cleaner | 29.5 |
| Stain Control ™ | 30.5 |
| Test Sample from Ex. 5 | 63.4 |

Since the surface tension of the prior art aqueous surfactant solutions are typically below 35 dynes/cm, it has been found that the standard soil repellent finishes on fiber surfaces such as carpets, upholstery and the like have been unable to prevent surfactant containing cleaning solutions from penetrating the soil repellent finishes applied on carpet surfaces resulting in several problems including the following:

1. As the stain/soil is emulsified and dispersed, instead of being removed, the stain/soil is carried deeper into the fiber, backing and padding of a carpet as the low energy of the fiber finish is overcome. This can actually cause the soil to appear to be removed, only to be discovered that the stain/soil has actually only migrated to the padding and will later often re-migrate back to the surface as the fiber dries (or during subsequent application of cleaner).

2. As the surfactant solution penetrates a carpet fiber, the visual appearance of the fiber is changed due to loss of twist and inflection of the angle of carpet pile. While all of the cleaners tested herein had some effect on the fiber pile, surfactant-containing cleaners caused greater fiber damage. The cleaning compositions of the present invention as produced in accordance with Example 5 caused less initial damage and the fibers had greater ability to recover to near original appearance. The loss of twist is accompanied by an increased loss of fiber, as mechanical force is applied to the carpet to remove stains and soil.

3. Once the surfactant solution has penetrated completely into the carpet fiber, backing and padding, the solution is more difficult to remove by either blotting or extraction. This results in longer drying times and decreased customer satisfaction.

The surfactant-free cleaning compositions of the present invention as exemplified by the compositions produced in accordance with the procedures set forth in Example 5 outperformed the prior art surfactant containing cleaning compositions which were tested such as the Control Samples set forth in Example 6. Also, when the stained areas discussed in Example 6 were cut away and inspected, it was noted that a significant portion of many stains in the Control Samples had migrated, spreading the stains out from the center to the base of the fiber strands and carpet backing.

Example 8

This Example demonstrated the use of the surfactant-free aqueous cleaning compositions of the present invention to clean carpeting and to illustrate the enhanced affect the use of these compositions has on the attraction of common dirt to a cleaned area of carpet fiber (i.e., to prevent re-soiling). Re-soiling performance of the compositions of this invention has been determined herein by application of the cleaning composition of Example 5 to test carpet and subsequent application of test soil, followed by vacuuming.

The re-soil testing procedure employed in this Example included adjusting the nozzle of a spray/steam/off trigger sprayer to a medium spray pattern (typically about 70% closed for an adjustable sprayer that can be adjusted anywhere from a fine mist through medium, coarse and, finally, to a stream spray pattern when fully opened). Then, 15 grams of each test carpet cleaning composition was sprayed onto an approximately 3" times 15" area of carpet (at an application rate of 0.3 grams per inch). After 3 minutes, the treated area was thoroughly blotted with paper towels (using one paper towel per 5 grams of cleaning composition applied). The carpet sample was then conditioned for 24 hours at 23° C. (about 70% relative humidity). Thereafter, a ⅛" layer of Scotts Potting Soil was applied evenly to the carpet sample and excess soil was shaken from the carpet. The results of this soil application to the previously cleaned carpet were observed and recorded employing the rating scale set forth below and then one-half of the re-soiled carpet was vacuumed by passing the a vacuum cleaner over the carpet surface three times and the vacuumed area of the re-soiled carpet was observed and graded utilizing the same rating scale set forth below. The results of this re-soil testing were as follows in Table 17.

TABLE 17

Resoiling Results

Cleaner Compositions

|  | Test Sample Cleaning Compositions from Ex. 1 | Resolve ® "Spot and Stain" (Control) | BISSELL "Tough Stain Precleaner"™ (Control) |
|---|---|---|---|
| Without Vacuuming | 1.0 | 0.5 | 1.0 |
| With Vacuuming | 4.0 | 3.5 | 3.0 |

Re-soil Rating:
5—no soil remaining
4—slight soil remaining
3—noticeable soil remaining
2—considerable soil remaining
1—severe soil remaining Based on visual observation and ratings of the re-soil testing, it was determined that the surfactant-free aqueous cleaning compositions of the present invention outperformed the commercially available prior art Control products. Also, when the soiled areas were closely inspected, it was noted that a significant level of imbedded soil was left under the surface of the carpet fiber when the Control products were applied to the carpet surface. It is believed that this imbedded soil resulted from the presence of surfactants in the Control products, thus having an adverse influence on the re-soil rating as compared with the surfactant-free cleaning compositions of the present invention which did not leave such imbedded soil under the surface of in the carpet fiber.

Example 9

To simulate the use of the surfactant-free aqueous cleaning compositions of the present invention to disperse common dirt and to demonstrate the improved dispersion achieved with the compositions of the present invention as compared with prior art commercial products, a 20 g test sample of the aqueous cleaning composition produced in Example 5 was introduced into a 24 mL KIMAX Sample Vial (VWR Cat #66010-429) along with a dirt sample comprising 0.2 g Georgia Red Clay which was obtained from a household yard and was prepared by air drying at 23 degree C. and 70% relative humidity and, then, grinding with a mortar and pestle. For purposes of providing control samples for comparative testing, two additional 20 g samples comprising two commercially available prior art cleaning products (i.e., one sample being prepared with RESOLVE®™ "Spot and Stain" and the other being prepared with BISSELL "Tough Stain Precleaner"™) were mixed with dirt samples in a similar manner in separate Sample Vials.

After the test sample and the control sample cleaning solutions and the dirt sample were introduced into the Sample Vials, the Sample Vials were each capped and held without shaking for 15 seconds. Then, each of the Sample Vials was inverted three times, followed by a 60 second holding period without shaking and then each of the Sample Vials was again inverted three times. Based on visual observations, the dispersion rate of the dirt in each of the tested cleaning solutions was determined and recorded after a 1 minute, a 15 minutes and a 60 minutes interval and is tabulated in Table 18.

TABLE 18

Soil Dispersion Results

Cleaner Compositions

| Time | Composition of Example 5 | Resolve ® "Spot and Stain" (Control) | BISSELL "Tough Stain Precleaner"™ (Control) |
|---|---|---|---|
| 1 Minute | 3.0 | 0.5 | 0.1 |
| 15 Minutes | 3.0 | 0.5 | 0.1 |
| 60 Minutes | 3.0 | 0.5 | 0.1 |

Soil Dispersion Rating:
5—100% dispersed
4—75% dispersed
3—50% dispersed
2—25% dispersed
0—0% dispersed As a result of the visual observation and ratings of this red clay dispersion testing, it was demonstrated that the cleaning compositions of the present invention significantly outperformed both of the commercially available, prior art control products tested in regard to dispersion properties—without the use of surfactants.

While the present invention has been described with reference to specific embodiments, examples and ranges, it will be clear to those skilled in the art that modification may be made without departing from the invention which is specifically set forth in the following claims.

REFERENCES

1. USEPA, Air Quality Criterion for Particulate Matter, Volumes I and II, http://cfpub.epa.gov/ncea/cfm/partmatt.cfm (October 2004)
2. USEPA, Child Exposure Factors Handbook, EPA-600-P-00-002B, (September 2002)
3. PTL (DRAFT)—Standard Test Practice Using X-Ray Fluorescence for Evaluating Cleaning Effectiveness of Carpet Cleaning Processes (2004)
4. ASTM D6540-00 Standard Test Method for Accelerated Soiling of Pile Yarn Floor Covering 5. R. Sporik et al., Mite, Cat and Cockroach Exposure, Allergen Sensitization, Asthma in Children: A Case-Control Study of Three Schools, Thorax 54:675 (1999)
6. J. C. T. Kwak, Editor: Polymer-Surfactant Systems; Marcel Dekker, New York, (1998).
7. E. D. Goddard and K. P. Anathapadhmanabhan, Editors; Interactions of Surfactants with Polymers and Proteins; CRC Press; Boca Raton, Fla. (1993).
8. J. Gauthire-Lafaye and R. Gresser; Polymers in Detergency, AOCS 4th World Congress on Dewtergents, Rhodia, Courbevoie, France (1998).
9. R. Nagarajan, Polymer-Surfactant Interactions, AOCS Presentation, Pennsylvania State University, (2001).
10. Mandeep Singh Bakshi; Surfactant-Polymer Interactions; Journal of Surfactants and detergents, vol. 4, No. 1; (January 2001).
11. Mandeep Singh Bakshi; Polymer-Induced Incompatibility in the Mixed Micelle Formation of Cationic Surfactants with Bulky Polar Head Groups; Journal of Surfactants and detergents, vol. 4, No. 3; (July 2001).
12. Donald H. Napper; Polymer Stabilization of Colloidal Dispersions. Colloid Science. (1983).

U.S. patents and patent applications

| Pat No. | Inventor | Pat No. | Inventor |
| --- | --- | --- | --- |
| 4035148 | Metzger et al. | 5928384 | Scialla et al. |
| 4203859 | Kirn et al. | 5962391 | Oldenhove. |
| 4925588 | Berrod et al. | 6019963 | Kling et al. |
| 5510047 | Gabriel et al. | 6171346 | Yeazell et al. |
| 5514302 | Brown | 6177395 | Silvaggi et al. |
| 5565145 | Watson et al. | 6274540 | Scheibel et al. |
| 5566145 | Sasaki. | 6403547 | Grippaudo et al. |
| 5643861 | de Guertechin et al. | 6407048 | Grippaudo et al. |
| 5718729 | Harris. | 6605579 | Arvanitidou et al. |
| 5904735 | Gutierrez et al. | 2003/0215470 | Wilmott et al. |
| 5905065 | Scialla et al. | | |

What is claimed is:

1. A method for lowering particulate matter in an interior environment, comprising,
   i) contacting an interior environment fiber or surface with a surfactant-free composition, having a surface tension of at least greater than about 38 dynes per centimeter and comprising,
      a) at least one dispersing agent;
      b) at least one anti-redeposition agent;
      c) at least one pH modifier;
      d) at least one chelating agent; and
      e) at least one stabilizing agent; and
   ii) removing a portion of the surfactant-free composition from the contacted interior environment fiber or surface after a time sufficient to disperse at least a portion of the total amount of particulate matter.

2. The method of claim 1, wherein the contacting and removing steps are performed more than one time.

3. The method of claim 1, wherein the composition further comprises at least one fragrance.

4. The method of claim 1, wherein the surfactant-free composition further comprises at least one preservative agent.

5. The method of claim 1, wherein the surfactant-free composition is a liquid having a surface tension greater than about 38 dynes per centimeter.

6. The method of claim 1, wherein the at least one dispersing agent is polyacrylic acid, polyacrylic acid/maleic acid copolymers; styrene/maleic anhydride copolymers, polymethacrylic acid, polyaspartic acid or combinations or mixtures thereof.

7. The method of claim 1, wherein the at least one anti-redeposition agent is polyvinylpyrrolidone; polyvinylbetaine; polyvinyl pyrrolidone/vinylacetate copolymers; polyvinylpyrrolidone/dimethylaminoethylmethacrylate copolymers; polyvinylpyrrolidone/acrylic acid copolymers; polymethylvinylether/maleic anhydride copolymers; polyvinylpyridine-n-oxide or combinations or mixtures thereof.

8. The method of claim 1, wherein the at least one pH modifier is a counter ion of sodium ions, potassium ions, calcium ions, magnesium ions, ammonium ions and amine ions or combinations or mixtures thereof.

9. The method of claim 1, wherein the at least one chelating agent is ethylenediaminetetraacetic acid; diethylenediaminepentaacetic acid; nitrilotriacetic acid; hydroxyethylenediaminetriacetic acid; iminodisuccinic acid; aminotrismethylenephosphonic acid; hexamethylenediaminetetramethylenephosphonic acid; diethylenetriaminepentamethylenephosphonic acid or combinations or mixtures thereof.

10. The method of claim 1, wherein the surfactant-free composition further comprises at least one fragrance and the at least one fragrance is terpene compounds; monocyclic terpenes; limonene; dicyclic terpenes; pinene; acyclic terpenes; myrcene; oxygenated alcohol, aldehyde, ester, ether or ketone terpene derivatives; oxygenated alcohol, aldehyde, ester, ether or ketone aromatic derivatives; oils derived from citrus peels; lemon oil, orange oil, time oil, tangerine oil, grapefruit oil; oils of eucalyptus globulos, oil of wintergreen, or combinations or mixtures thereof.

11. The method of claim 1, wherein the at least one stabilizing agent is alcohols, methyl alcohol, ethyl alcohol, isopropyl alcohol, propyl alcohol, glycol ethers, methyl glycol ethers, ethyl glycol ethers, propyl glycol ethers, isopropyl glycol ethers, butyl glycol ethers, phenyl glycol ethers, ethylhexyl ethers; glycol ether esters of glycols, ethylene glycol, diethylene glycol, triethylene glycol, propylene glycol, dipropylene glycol, tripropylene glycol, diethylene glycol monobutylether, diethylene glycol monobutylether acetate, or combinations or mixtures thereof.

12. The method of claim 1, wherein the amount of pH modifier present in the composition is sufficient to maintain a pH range of about 5.0 to about 12.0 in the liquid composition.

13. The method of claim 4, wherein the at least one preservative agent is 1,3-dihydroxymethyl-5-5-dimethylhydantoin (DMDM Hydantoin); 1,2-benzisothiazolin-3-one; 5-chloro-2-methyl-4-isothiazolin-3-one; 2-methyl-4-isothiazolin-3-one; 3-iodo-2-propynyl butyl carbamate; phenoxyethanol; 2-bromo-2-nitropropane-1,3-diol; methyl paraben; propyl paraben; isopropyl paraben; butyl paraben; isobutyl paraben; diazolidinyl urea and hydroxymethylglycinate or combinations or mixtures thereof.

14. A method for removing allergens from interior environments, comprising,
   i) contacting an interior environment fiber or surface with a surfactant-free composition having a surface tension of greater than about 38 dynes per centimeter, comprising,
      a) at least one dispersing agent;
      b) at least one anti-redeposition agent;
      c) at least one pH modifier;
      d) at least one chelating agent; and
      e) at least one stabilizing agent; and ii) removing a portion of the surfactant-free composition from the contacted interior environment fiber or surface after a time sufficient to disperse at least a portion of the total amount of particulate matter comprising allergens.

15. The method of claim 14, wherein the surfactant-free composition further comprises at least one preservative agent.

16. The method of claim 14, wherein the applying and removing steps are performed more than one time.

17. The method of claim 14, wherein the surfactant-free composition further comprises at least one fragrance.

* * * * *